(12) United States Patent
Finberg et al.

(10) Patent No.: US 9,271,972 B2
(45) Date of Patent: Mar. 1, 2016

(54) COMPOUNDS FOR MODULATING TLR2

(71) Applicant: University of Massachusetts, Boston, MA (US)

(72) Inventors: Robert W. Finberg, Sudbury, MA (US); Evelyn A. Kurt-Jones, Belmont, MA (US); Shenghua Zhou, Shrewsbury, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 14/079,809

(22) Filed: Nov. 14, 2013

(65) Prior Publication Data

US 2014/0296219 A1    Oct. 2, 2014

Related U.S. Application Data

(63) Continuation of application No. 12/948,556, filed on Nov. 17, 2010, now Pat. No. 8,609,663.

(60) Provisional application No. 61/262,400, filed on Nov. 18, 2009.

(51) Int. Cl.

| | |
|---|---|
| *A61K 31/423* | (2006.01) |
| *A61K 31/454* | (2006.01) |
| *A61K 31/4725* | (2006.01) |
| *A61K 31/496* | (2006.01) |
| *A61K 31/42* | (2006.01) |
| *A61K 31/4245* | (2006.01) |
| *A61K 31/505* | (2006.01) |
| *A61K 31/551* | (2006.01) |
| *A61K 31/429* | (2006.01) |
| *A61K 31/443* | (2006.01) |
| *A61K 31/4433* | (2006.01) |
| *A61K 31/4439* | (2006.01) |
| *A61K 31/4535* | (2006.01) |
| *A61K 31/4745* | (2006.01) |
| *A61K 31/506* | (2006.01) |

(52) U.S. Cl.
CPC ............... *A61K 31/454* (2013.01); *A61K 31/42* (2013.01); *A61K 31/423* (2013.01); *A61K 31/429* (2013.01); *A61K 31/4245* (2013.01); *A61K 31/443* (2013.01); *A61K 31/4433* (2013.01); *A61K 31/4439* (2013.01); *A61K 31/4535* (2013.01); *A61K 31/4725* (2013.01); *A61K 31/4745* (2013.01); *A61K 31/496* (2013.01); *A61K 31/505* (2013.01); *A61K 31/506* (2013.01); *A61K 31/551* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | |
| 5,464,863 A | 11/1995 | Nagamine et al. | |
| 5,908,842 A | 6/1999 | Guthikonda et al. | |
| 2004/0052822 A1 | 3/2004 | Kohara et al. | |
| 2005/0043347 A1 * | 2/2005 | Betschmann et al. | ........ 514/301 |
| 2006/0261952 A1 | 11/2006 | Kavounas et al. | |
| 2007/0032522 A1 | 2/2007 | Kumar et al. | |
| 2007/0254934 A1 | 11/2007 | Hruby et al. | |
| 2008/0009543 A1 | 1/2008 | Ducoux et al. | |
| 2008/0090788 A1 | 4/2008 | Packham et al. | |
| 2008/0261952 A1 | 10/2008 | Bloxham et al. | |
| 2008/0261965 A1 * | 10/2008 | Flynn | ................... C07D 401/14 514/230.5 |

FOREIGN PATENT DOCUMENTS

WO    WO 2008/109154    9/2008

OTHER PUBLICATIONS

International Search Report and Written Opinion in International Application No. PCT/US2010/056974, dated Aug. 2, 2011, 12 pages.
International Preliminary Report on Patentability in International Application No. PCT/US2010/056974, dated May 31, 2012, 8 pages.
Berge, et al., "Pharmaceutical Salts," *J. Pharm. Sci*, 1977, 66(1):1-19.
Brehm, et al., "T cell immunodominance and maintenance of memory regulated by unexpectedly cross-reactive pathogens," *Nat, Immunol.*, 2002, 3(7):627-34.
Brown et al., "R753Q single-nucleotide polymorphism impairs toll-like receptor 2 recognition of hepatitis C virus core and nonstructural 3 proteins," *Transplantation*, 2010, 89(7):811-5.
Compton, et al., "Human Cytomegalovirus Activates Inflammatory Cytokine Responses via CD14 and Toll-Like Receptor 2," *J. of Virology*, 2003, 77(8):4588-4596.
Czarnecki, et al., "Small Molecule Modulators of Toll-like Receptors," *J. Med. Chem.*, 2008, 51(21):6621-6626.
Delaloye et al., "Innate Immune Sensing of Modified Vaccinia Virus Ankara (MVA) is Mediated by TLR2-TLR6, MDA-5 and the NALP3 Inflammasome," *PLoS Pathogens*, Jun. 2009, 5(6):1-15.
Djavani et al., "Early Blood Profiles of Virus Infection in a Monkey Model for Lassa Fever," *J Virol.*, 2007, 81(15):7960-7973.
Finberg, et al., "Toll like receptors and viruses," *Rev. Med. Virol.*, 2007, 17:35-43.
Hornug et al., "Sequence-specific potent induction of IFN-α by short interfering RNA in plasmacytoid dendritic cells through $TLR_7$," *Nat. Med.*, 2005, 11(3):263-70.
Huff, J. Med. Chem. 34(8) (1991), pp. 2305-2314.
Kurt-Jones et al., "Herpes simplex virus 1 interaction with Toll-like receptor 2 contributes to lethal encephalitis," *Proc Natl Acad Sci USA*, Feb. 2004, 101(5): 1315-20.
Kurt-Jones et al., "The role of toll-like receptors in herpes simplex infection in neonates," *J Infect Dis.*, Mar. 2005, 191(5):746-8.

(Continued)

*Primary Examiner* — Alicia L Otton
(74) *Attorney, Agent, or Firm* — Fish & Richardson P.C.

(57) ABSTRACT

The present invention is directed to methods, kits, and uses of inhibitors of LCMV mediated NF-κB activation to treat viral infections and inflammatory conditions.

22 Claims, 22 Drawing Sheets

(56) References Cited

OTHER PUBLICATIONS

Lee et al., "Influenza A Viruses Upregulate Neutrophil Toll-Like Receptor 2 Expression and Function," *Scandinavian J Immunol.*, 2006, 63:81-89.
Linero et al., "Host Cell Factors as Antiviral Targets in Arenavirus Infection," *Viruses*, 2012, 4:1569-1591.
Mandell, et al., "Intact Gram-Negative Helicobacter pylon, Helicobacter felis, and Helicobacter hepaticus Bacteria Activate Innate Immunity via Toll-Like Receptor 2 but Not Toll-Like Receptor 4," *Infection and Immunity*, 2004, 72(11):6446-6454.
Murawski et al., "Respiratory syncytial virus activates innate immunity through Toll-like receptor 2," *J Virol.*, Feb. 2009, 83(3):1492-500.
Nikula et al. "Animal Models of Chronic Bronchitis and Their Relevance to Studies of Particle-induced Disease," *Inhal. Toxicol.*, 2000, 12(Suppl. 4):123-53.
Ravin, Louis J., "Preformulation", Remington's Pharmaceutical Sciences, 17th ed., Mack Publishing Company, Easton, Pa., 1985, Chapter 76, pp. 1409-1423.
Sonderstrup, "Development of humanized mice as a model of inflammatory arthritis," *Springer Sem. Immunopathol.*, 2003, 25:35-45
Szomolanyi-Tsuda et al., "Role for TLR2 in NK cell-mediated control of murine cytomegalovirus in vivo," *J Virol.*, May 2006, 80(9):4286-91.
Thompson et al., "Pattern Recognition Receptors and the Innate Immune Response to Viral Infection," *Viruses*, 2011, 3:920-940.

van Lint et al., "Herpes simplex virus immediate-early ICP0 protein inhibits Toll-like receptor 2-dependent inflammatory responses and NF-kappaB signaling," *J Virol.*, Oct. 2010, 84(20):10802-11.
Wang et al., "Role of specific innate immune responses in herpes simplex virus infection of the central nervous system," *J Virol.*, Feb. 2012, 86(4):2273-81.
Wang et al., "Varicella-zoster virus activates inflammatory cytokines in human monocytes and macrophages via Toll-like receptor 2," *J Virol.*, Oct. 2005, 79(20):12658-66.
Zhou et al., "Discovery of a novel TLR2 signaling inhibitor with anti-viral activity," *Antiviral Res.*, Sep. 2010, 87(3):295-306
Zhou et al., "Lymphocytic choriomeningitis virus (LCMV) infection of CNS glial cells results in TLR2-MyD88/Mal-dependent inflammatory responses," *J Neuroimmunol.*, Feb. 2008, 194(1-2):70-82.
Zhou et al., "MyD88 is critical for the development of innate and adaptive immunity during acute lymphocytic choriomeningitis virus infection," *Eur. J. Immunol.*, 2005, 35(3):822-30.
Cario, E., "Barrier-protective function of intestinal epithelial Toll-like receptor 2", Mucosal Immunology, vol. 1 (Supplement 1):S62-S67 (2008).
Frasnelli et al., "TLR2 modulates inflammation in zymosan-induced arthritis in mice", Arthritis Res Ther., vol. 7:R370-R379 (2005).
Obonyo et al., "Deficiencies of Myeloid Differentiation Factor 88, Toll-Like Receptor 2 (TLR2), or TLR4 Produce Specific Defects in Macrophage Cytokine Secretion Induced by *Helicobacter pylori*V", Infection and Immunity, vol. 75:2408-2414 (2007).
Péne et al., "Toll-Like Receptors 2 and 4 Contribute to Sepsis-Induced Depletion of Spleen Dendritic CellsV", Infection and Immunity, vol. 77:5651-5658 (2009).

\* cited by examiner

A (Primary screening)

B (Cherry-Pick)

C

D

COMPOUNDS FOR MODULATING TLR2

This application is a continuation of U.S. Ser. No. 12/948,556, filed Nov. 17, 2010, which claims the benefit of priority of U.S. Prov. Appl. No. 61/262,400, filed Nov. 18, 2009, which is incorporated by reference in its entirety.

FEDERALLY SPONSORED RESEARCH OR DEVELOPMENT

This invention was made with Government support under Grant No U54AI057159 awarded by the National Institutes of Health. The Government has certain rights in the invention.

TECHNICAL FIELD

The present invention involves methods, kits, and uses of inhibitors of lymphocytic choriomeningitis virus (LCMV)-mediated NF-κB activation to treat viral infections and inflammatory conditions.

BACKGROUND

Toll-like receptors (TLRs), a family of important innate immune molecules, are expressed both on the cell surface and in intracellular compartments of many immune and non-immune cells. TLRs are one of the best characterized innate pathogen recognition receptors (PRR). TLRs are transmembrane proteins which function as pattern recognition receptors for the detection and response to microbial ligands. To date, 10 TLRs have been identified in humans and 11 in mice. Natural or synthetic ligands for at least 9 TLRs have been identified. Activation of TLRs results in the recruitment of adaptor proteins including MyD88 (most TLRs except TLR3), TRIF (for TLR3 and TLR4), and Mal/TIRAP (TLR2 and TLR4) to the TIR domain. A series of phosphorylation/recruitment/activation events leads to the activation and translocation of the transcription factors nuclear factor-κB (NF-κB) NF-κB to the nucleus and the transcription of inflammatory and anti-inflammatory cytokine genes. While TLR induced innate immune responses help clear viral infections, TLRs have also been implicated in the immunopathology of virus infection. It is thought that TLR-mediated inflammatory response in response to viruses might contribute to diseases. In particular, it has been found that TLR2, TLR3, and TLR7 are involved in viral-associated immunopathology. Thus, in some circumstances, blockade of TLR-mediated signaling pathway may protect the host from the harmful inflammatory responses.

Although originally described as receptors for bacteria and fungi, it has now become clear that TLRs mediate the production of cytokines in response to a variety of viruses and viral ligands. A role for the Toll-like receptors, TLR2, TLR3, TLR4, TLR7 and TLR9, in the response to viruses has been established. Previous experiments have demonstrated that the cytokine response to human cytomegalovirus (CMV) and Herpes simplex virus-1 (HSV) is controlled by TLR2, while the response to respiratory syncytial virus (RSV) is dependent on TLR4 (13-15, 20). Previous studies have demonstrated that Lymphocytic choriomeningitis virus (LCMV) infection induces the activation of transcription factor nuclear factor-kappaB (NF-κB) and inflammatory responses through a TLR2/TLR6/CD14-MyD88/Mal-dependent signaling pathway. LCMV is the prototypic virus of the arenavirus family. Several members in the arenavirus family, including Lassa hemorrhagic fever (HF) virus and Argentine HF virus, cause severe, often lethal, viral hemorrhagic fevers in humans. Moreover, HF viruses have recently received considerable scrutiny because of the potential use of arenaviruses as biological weapons for bioterrorism (see the world wide web at bt.cdc.gov/agent/vhf).

Inhibiting TLR signaling in LCMV infected cells could have great therapeutic potential, not only in the treatment of LCMV disease (an arenavirus prototypic of the response to hemorrhagic fever viruses), but also in the treatment of other viral diseases involving TLR activation, including herpes encephalitis (HSV-1), genital herpes (HSV-2) and cytomegalovirus infection.

For example, ribavirin, a member of the nucleoside antimetabolite drugs that interfere with duplication of viral genetic material, is active against a number of DNA and RNA viruses, including hemorrhagic fever viruses; however, due to its side-effects, such as dose-dependent inhibiting effect on DNA synthesis, hemolytic anemia, and significant teratogenic effects, its application in clinical is limited. Accordingly, there is a need to develop new compounds that inhibit LCMV-induced NF-κB activation and cytokine responses through either modulating TLR2 expression or blocking LCMV replication. This invention addresses this need and others.

SUMMARY

LCMV has been used as a model to screen compounds that particularly target the TLR2-mediated signaling pathway. A human embryonic kidney (HEK) cell line stably expressing human TLR2, CD14, and NF-κB-driven firefly luciferase has been established and used to screen over 100,000 small molecule compounds from compound libraries. A number of candidates have been identified having the ability to specifically inhibit LCMV-induced cytokine production. Certain of these compounds inhibit LCMV-induced NF-κB activation and cytokine responses through either modulating TLR2 expression or blocking LCMV replication.

Accordingly, the present invention provides, inter alia, methods of treating a viral infection or inflammatory condition in an individual in need thereof, comprising administering a therapeutically effective amount of an agent to the individual, wherein the agent is selected from a compound of Formulas I to IX, or a pharmaceutically acceptable salt thereof.

The present invention further provides uses of the compounds for the preparation of medicaments and kits comprising the compounds for use in treatment of treatment of a viral infections or inflammatory condition in an individual in need thereof. The present invention further provides the compounds for use in treatment of viral infections or inflammatory conditions.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A and 1B depict flow cytometry staining with anti-human TLR2 antibody (clone 11G7) (FIG. 1A) and CD14 (FIG. 1B).

FIG. 1C depicts NF-kB activity (luminescence) determined by luciferase assay after SZ10 cells were challenged with medium, LCMV-Arm, uninfected BHK-21 cell supernatant, TNF-α (non-TLR stimulant), and $Pam_2CSK_4$ (TLR2 ligand).

DETAILED DESCRIPTION

Figure 1:
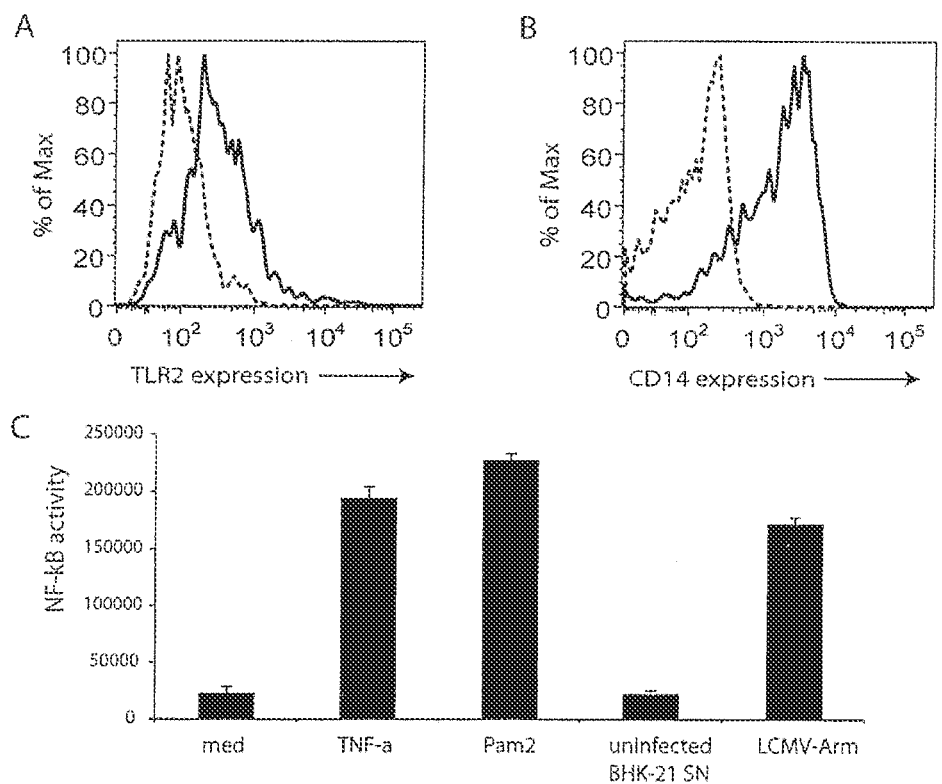

The present invention provides, inter alia, a method of treating a viral infection or inflammatory condition in an individual in need thereof, comprising administering a therapeutically effective amount of an agent to the individual, wherein the agent is selected from a compound of Formulas I-IX, or a pharmaceutically acceptable salt thereof. In some embodiments, the viral infection is selected from Tacaribe virus, Rift Valley Fever Virus, herpes simplex virus-1 (HSV-1), herpes simplex virus-2 (HSV-2), lymphocytic choriomenigitis virus (LCMV), human cytomegalovirus (HCMV), respiratory syncytial virus (RSV), vesicular stomatitis virus (VSV), varicella zoster virus (VZV), influenza, Lassa hemorrhagic fever (HF), Argentine HF virus, West Nile virus, reovirus, Coxsackie B virus, papillomavirus, measles, and viral encephalitis.

Other conditions that can be treated by the methods described herein include, but are not limited to, viral infections and undesirable activation of the innate immune system (e.g., undesirable inflammation). In some embodiments, the conditions include fungal infections, tuberculosis, leprosy, bone resorption (e.g., in periodontal disease), and arthritis (e.g., associated with Lyme disease). In some embodiments, the inflammatory condition is selected from chronic joint disease, chronic active gastritis, chronic mucosal inflammation, and sepsis.

In some embodiments, the present invention provides a compound of any one of Formulas I-IX, or a pharmaceutically acceptable salt thereof.

The present invention further provides use of an agent (compounds of Formulas I-IX, or embodiments thereof) for use in a method of treatment of a viral infection or inflammatory condition in an individual in need thereof.

The present invention also provides an agent (compounds of Formulas I-IX, or embodiments thereof) for use in a method of treatment of a viral infection of inflammatory condition in an individual in need thereof.

The present invention further provides kits comprising:
a compound of Formulas I-IX, or embodiments thereof; and
instructions;
wherein said instructions comprise a direction to administer a therapeutically effective amount of a compound of Formula I-IX to an individual in need of treatment of a viral infection or inflammatory condition.

In some embodiments, the present invention provides a pharmaceutical composition comprising a compound of Formulas I-IX, or embodiments thereof, and a pharmaceutically acceptable carrier. In some embodiments, the composition is used for treatment of any of the disorders described herein.

In some embodiments, the agent is a compound of Formula I:

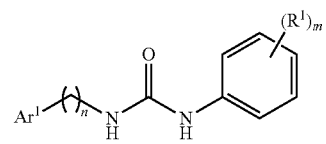

or a pharmaceutically acceptable salt thereof, wherein:
Ar$^1$ is a 5- or 6-membered heteroaryl ring, which is optionally fused to a phenyl ring; wherein Ar$^1$ is optionally substituted with p independently selected R$^2$ groups;
each R$^1$ is independently selected from —OR$^a$, —SR$^b$, —C(O)R$^b$, —C(O)NR$^e$R$^f$, —C(O)OR$^a$, —OC(O)R$^b$, —OC(O)NR$^e$R$^f$, —NR$^e$R$^f$, —NR$^c$C(O)R$^d$, —NR$^c$C(O)OR$^d$, —NR$^c$C(O)NR$^d$, —S(O)R$^b$, —S(O)NR$^e$R$^f$, —S(O)$_2$R$^a$, —NR$^c$S(O)$_2$R$^d$, halogen, cyano, nitro, C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, $C_{6-10}$ aryl-$C_{1-3}$ alkyl, $C_{1-9}$ heteroaryl, and $C_{1-9}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-9}$ heterocycloalkyl, $C_{2-9}$ heterocycloalkyl-$C_{1-3}$ alkyl, $C_{6-10}$ aryl, $C_{6-10}$ aryl-$C_{1-3}$ alkyl, $C_{1-9}$ heteroaryl, and $C_{1-9}$ heteroaryl-$C_{1-3}$ alkyl are each optionally substituted by 1, 2, 3, or 4 independently selected $R^{1'}$ groups;

each $R^2$ is independently selected from —$OR^m$, —$SR^n$, —$C(O)R^n$, —$C(O)NR^qR^r$, —$C(O)OR^m$, —$OC(O)R^n$, —$OC(O)NR^qR^r$, —$NR^qR^r$, —$NR^cC(O)R^p$, —$NR^cC(O)OR^p$, —$NR^cC(O)NR^n$, —$S(O)R^n$, —$S(O)NR^qR^p$, —$S(O)_2R^m$, —$NR^cS(O)_2R^p$, halogen, cyano, nitro, $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-9}$ heterocycloalkyl, $C_{2-9}$ heterocycloalkyl-$C_{1-3}$ alkyl, $C_{6-10}$ aryl, $C_{6-10}$ aryl-$C_{1-3}$ alkyl, $C_{1-9}$ heteroaryl, and $C_{1-9}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, $C_{3-10}$ cycloalkyl, $C_{3-10}$ cycloalkyl-$C_{1-3}$ alkyl, $C_{2-9}$ heterocycloalkyl, $C_{2-9}$ heterocycloalkyl-$C_{1-3}$ alkyl, $C_{6-10}$ aryl, $C_{640}$ aryl-$C_{1-3}$ alkyl, $C_{1-9}$ heteroaryl, and $C_{1-9}$ heteroaryl-$C_{1-3}$ alkyl are each optionally substituted by 1, 2, 3, or 4 independently selected $R^{2'}$ groups;

each $R^b$ and $R^n$ is independently selected from $C_{1-6}$ alkyl, $C_{2-6}$ alkenyl, $C_{2-6}$ alkynyl, $C_{1-6}$ haloalkyl, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl are each optionally substituted by 1, 2, 3, or 4 independently selected $R^g$ groups;

each $R^a$, $R^c$, $R^d$, $R^e$, $R^f$, $R^m$, $R^o$, $R^p$, $R^r$, and $R^q$ is independently selected from H, $C_{1-6}$ alkyl, $C_{2-6}$ alkenyl, $C_{2-6}$ alkynyl, $C_{1-6}$ haloalkyl, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl are each optionally substituted by 1, 2, 3, or 4 independently substituted $R^g$ groups;

each $R^{1'}$, $R^{2'}$, and $R^g$ is independently selected from halogen, cyano, nitro, hydroxyl, carboxy, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{1-4}$ alkylcarbonyl, $C_{1-4}$ alkoxycarbonyl, amino, $C_{1-4}$ alkylamino, di-$C_{1-4}$ alkylamino, and $C_{1-4}$ alkylsulfonyl;

n is an integer selected from 0, 1, and 2; and m and p are each independently an integer selected from 0, 1, 2, 3, 4, and 5; provided that the proper valencies are not exceeded.

In some embodiments, $Ar^1$ is selected from:

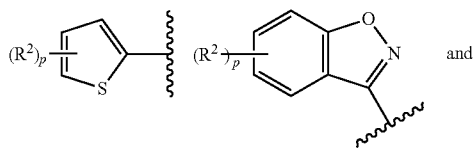

-continued

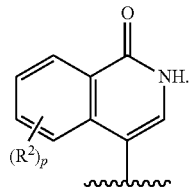

In some embodiments, $Ar^1$ is selected from:

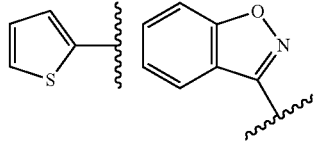

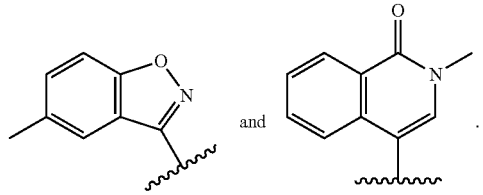

In some embodiments, $Ar^1$ is:

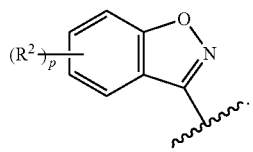

In some embodiments, each $R^2$ is independently selected from halogen, cyano, nitro, hydroxyl, carboxy, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{1-4}$ alkylcarbonyl, $C_{1-4}$ alkoxycarbonyl, amino, $C_{1-4}$ alkylamino, di-$C_{1-4}$ alkylamino, and $C_{1-4}$ alkylsulfonyl. In some embodiments, each $R^2$ is independently selected from $C_{1-6}$ alkyl. In some embodiments, each $R^2$ is independently selected from methyl.

In some embodiments, each $R^1$ is independently selected from —$OR^a$, —$C(O)R^b$, —$C(O)NR^eR^f$, —$C(O)OR^a$, —$NR^eR^f$, —$NR^cC(O)R^d$, —$S(O)_2R^a$, halogen, cyano, nitro, $C_{1-6}$ alkyl, $C_{1-6}$ haloalkyl, $C_{3-10}$ cycloalkyl, $C_{3-10}$ cycloalkyl-$C_{1-3}$ alkyl, $C_{2-9}$ heterocycloalkyl, and $C_{2-9}$ heterocycloalkyl-$C_{1-3}$ alkyl; wherein said $C_{1-6}$ alkyl, $C_{1-6}$ haloalkyl, $C_{3-10}$ cycloalkyl, $C_{3-10}$ cycloalkyl-$C_{1-3}$ alkyl, $C_{2-9}$ heterocycloalkyl, and $C_{2-9}$ heterocycloalkyl-$C_{1-3}$ alkyl are each optionally substituted by 1, 2, 3, or 4 independently selected $R^{1'}$ groups. In some embodiments, each $R^1$ is independently selected from —$OR^a$, —$C(O)OR^a$, halogen, $C_{1-6}$ haloalkyl, $C_{2-9}$ heterocycloalkyl, and $C_{2-9}$ heterocycloalkyl-$C_{1-3}$ alkyl, wherein said $C_{2-9}$ heterocycloalkyl, and $C_{2-9}$ heterocycloalkyl-$C_{1-3}$ alkyl are each optionally substituted with 1, 2, 3, or 4 independently selected $R^{1'}$ groups. In some embodiments, each $R^1$ is independently selected from chloro, trifluoromethyl, methoxy, methoxycarbonyl, 4-methylpiperazinyl, and (4-methylpiperidinyl)methyl.

In some embodiments, each $R^a$ is independently selected from H and $C_{1-6}$ alkyl.

In some embodiments, each $R^{1'}$ is independently $C_{1-4}$ alkyl.

In some embodiments, m is 0, 1, or 2. In some embodiments, n is 0. In some embodiments, n is 1. In some embodiments, p is 0 or 1.

In some embodiments, when $R^1$ is substituted $C_{1-6}$ alkyl, then each $R^{1'}$ is other than amino, $C_{1-4}$ alkylamino, or di-$C_{1-4}$ alkylamino.

In some embodiments:
$Ar^1$ is selected from:

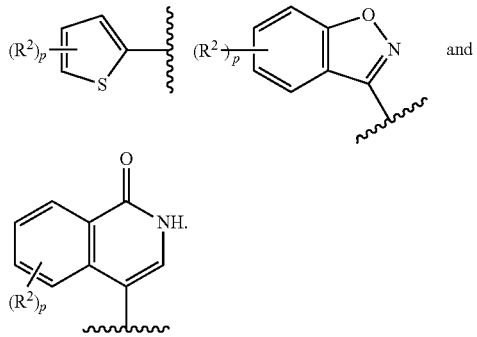

each $R^2$ is independently selected from halogen, cyano, nitro, hydroxyl, carboxy, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{1-4}$ alkylcarbonyl, $C_{1-4}$ alkoxycarbonyl, amino, $C_{1-4}$ alkylamino, di-$C_{1-4}$ alkylamino, and $C_{1-4}$ alkylsulfonyl;

each $R^1$ is independently selected from —$OR^a$, —$C(O)R^b$, —$C(O)NR^eR^f$, —$C(O)OR^a$, —$NR^eR^f$, —$NR^eC(O)R^d$, —$S(O)_2R^a$, halogen, cyano, nitro, $C_{1-6}$ alkyl, $C_{1-6}$ haloalkyl, $C_{3-10}$ cycloalkyl, $C_{3-10}$ cycloalkyl-$C_{1-3}$ alkyl, $C_{2-9}$ heterocycloalkyl, and $C_{2-9}$ heterocycloalkyl-$C_{1-3}$ alkyl; wherein said $C_{1-6}$ alkyl, $C_{1-6}$ haloalkyl, $C_{3-10}$ cycloalkyl, $C_{3-10}$ cycloalkyl-$C_{1-3}$ alkyl, $C_{2-9}$ heterocycloalkyl, and $C_{2-9}$ heterocycloalkyl-$C_{1-3}$ alkyl are each optionally substituted by 1, 2, 3, or 4 independently selected $R^{1'}$ groups;

each $R^{1'}$ is independently $C_{1-4}$ alkyl;
m is 0, 1, or 2;
n is 0 or 1; and
p is 0 or 1.

In some embodiments:
$Ar^1$ is selected from:

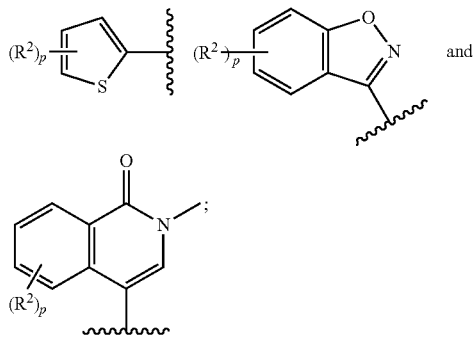

each $R^2$ is independently selected from $C_{1-6}$ alkyl;
each $R^1$ is independently selected from —$OR^a$, —$C(O)OR^a$, halogen, $C_{1-6}$ haloalkyl, $C_{2-9}$ heterocycloalkyl, and $C_{2-9}$ heterocycloalkyl-$C_{1-3}$ alkyl, wherein said $C_{2-9}$ heterocycloalkyl, and $C_{2-9}$ heterocycloalkyl-$C_{1-3}$ alkyl are each optionally substituted with 1, 2, 3, or 4 independently selected $R^{1'}$ groups;

each $R^{1'}$ is independently $C_{1-4}$ alkyl;
each $R^a$ is independently selected from H and $C_{1-6}$ alkyl;
m is 0, 1, or 2;
n is 0 or 1; and
p is 0 or 1.

In some embodiments:
$Ar^1$ is selected from:

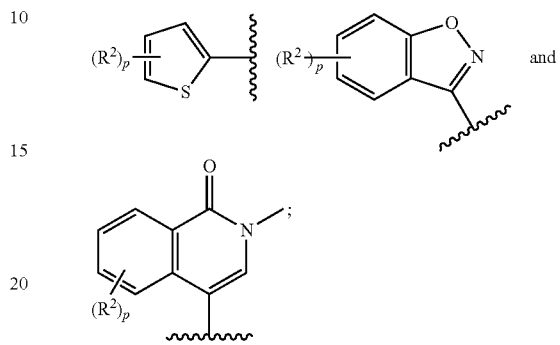

each $R^2$ is independently selected from methyl;
each $R^1$ is independently selected from chloro, trifluoromethyl, methoxy, methoxycarbonyl, 4-methylpiperazinyl, and (4-methylpiperidinyl)methyl;
m is 0, 1, or 2;
n is 0 or 1; and
p is 0 or 1.

In some embodiments, the compound is selected from:
1-(benzo[d]isoxazol-3-ylmethyl)-3-(4-((4-methylpiperidin-1-yl)methyl)phenyl)urea;
1-((5-methylbenzo[d]isoxazol-3-yl)methyl)-3-(4-((4-methylpiperidin-1-yl)methyl)phenyl)urea;
1-((5-methylbenzo[d]isoxazol-3-yl)methyl)-3-(3-(trifluoromethyl)phenyl)urea;
1-(3-chlorophenyl)-3-(benzo[d]isoxazol-3-ylmethyl)urea;
1-(benzo[d]isoxazol-3-ylmethyl)-3-(3-methoxyphenyl)urea;
methyl 4-(3-(benzo[d]isoxazol-3-ylmethyl)ureido)benzoate;
1-(4-((4-methylpiperidin-1-yl)methyl)phenyl)-3-(thiophen-2-yl)urea;
1-(2-methyl-1-oxo-1,2-dihydroisoquinolin-4-yl)-3-(4-((4-methylpiperidin-1-yl)methyl)phenyl)urea; and
1-((5-methylbenzo[d]isoxazol-3-yl)methyl)-3-(2-(4-methylpiperazin-1-yl)phenyl)urea;
or a pharmaceutically acceptable salt thereof.

In some embodiments, the agent is a compound of Formula II:

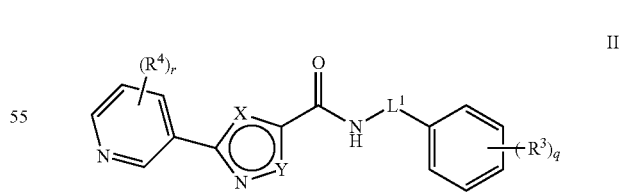

or a pharmaceutically acceptable salt thereof; wherein:
X is N and Y is O; or
X is O and Y is N;
$L^1$ is straight chain $C_{2-4}$ alkylene; which is optionally substituted by 1, 2, 3, or 4 groups independently selected from $C_{1-4}$ alkyl;
each $R^3$ is independently selected from —$OR^a$, —$SR^b$, —$C(O)R^b$, —$C(O)NR^eR^f$, —$C(O)OR^a$, —$OC(O)R^b$, —OC(O)NR$^e$R$^f$, —NR$^e$R$^f$, —NR$^c$C(O)R$^d$, —NR$^c$C(O)OR$^d$, —NR$^c$C(O)NR$^d$, —S(O)R$^b$, —S(O)NR$^e$R$^f$, —S(O)$_2$R$^a$, —NR$^c$S(O)$_2$R$^d$, halogen, cyano, nitro, C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl; wherein said C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl are each optionally substituted by 1, 2, 3, or 4 independently selected R$^{3'}$ groups;

each R$^4$ is independently selected from —OR$^m$, —SR$^n$, —C(O)R$^n$, —C(O)NR$^q$R$^r$, —C(O)OR$^m$, —OC(O)R$^n$, —OC(O)NR$^q$R$^r$, —NR$^q$R$^r$, —NR$^c$C(O)R$^p$, —NR$^c$C(O)OR$^p$, —NR$^c$C(O)NR$^p$, —S(O)R$^n$, —S(O)NR$^q$R$^p$, —S(O)$_2$R$^m$, —NR$^o$S(O)$_2$R$^p$, halogen, cyano, nitro, C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl; wherein said C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl are each optionally substituted by 1, 2, 3, or 4 independently selected R$^{4'}$ groups;

each R$^b$ and R$^n$ is independently selected from C$_{1-6}$ alkyl, C$_{2-6}$ alkenyl, C$_{2-6}$ alkynyl, C$_{1-6}$ haloalkyl, C$_{3-7}$ cycloalkyl, C$_{3-7}$ cycloalkyl-C$_{1-3}$ alkyl, C$_{2-6}$ heterocycloalkyl, C$_{2-6}$ heterocycloalkyl-C$_{1-3}$ alkyl, phenyl, phenyl-C$_{1-3}$ alkyl, C$_{1-6}$ heteroaryl, and C$_{1-6}$ heteroaryl-C$_{1-3}$ alkyl; wherein said C$_{1-6}$ alkyl, C$_{2-6}$ alkenyl, C$_{2-6}$ alkynyl, C$_{1-6}$ haloalkyl, C$_{3-7}$ cycloalkyl, C$_{3-7}$ cycloalkyl-C$_{1-3}$ alkyl, C$_{2-6}$ heterocycloalkyl, C$_{2-6}$ heterocycloalkyl-C$_{1-3}$ alkyl, phenyl, phenyl-C$_{1-3}$ alkyl, C$_{1-6}$ heteroaryl, and C$_{1-6}$ heteroaryl-C$_{1-3}$ alkyl are each optionally substituted by 1, 2, 3, or 4 independently selected R$^g$ groups;

each R$^a$, R$^c$, R$^d$, R$^e$, R$^f$, R$^m$, R$^o$, R$^p$, R$^r$, and R$^q$ is independently selected from H, C$_{1-6}$ alkyl, C$_{2-6}$ alkenyl, C$_{2-6}$ alkynyl, C$_{1-6}$ haloalkyl, C$_{3-7}$ cycloalkyl, C$_{3-7}$ cycloalkyl-C$_{1-3}$ alkyl, C$_{2-6}$ heterocycloalkyl, C$_{2-6}$ heterocycloalkyl-C$_{1-3}$ alkyl, phenyl, phenyl-C$_{1-3}$ alkyl, C$_{1-6}$ heteroaryl, and C$_{1-6}$ heteroaryl-C$_{1-3}$ alkyl; wherein said C$_{1-6}$ alkyl, C$_{2-6}$ alkenyl, C$_{2-6}$ alkynyl, C$_{1-6}$ haloalkyl, C$_{3-7}$ cycloalkyl, C$_{3-7}$ cycloalkyl-C$_{1-3}$ alkyl, C$_{2-6}$ heterocycloalkyl, C$_{2-6}$ heterocycloalkyl-C$_{1-3}$ alkyl, phenyl, phenyl-C$_{1-3}$ alkyl, C$_{1-6}$ heteroaryl, and C$_{1-6}$ heteroaryl-C$_{1-3}$ alkyl are each optionally substituted by 1, 2, 3, or 4 independently selected R$^g$ groups;

each R$^{3'}$, R$^{4'}$, and R$^g$ is independently selected from halogen, cyano, nitro, hydroxyl, carboxy, C$_{1-4}$ alkyl, C$_{1-4}$ haloalkyl, C$_{1-4}$ alkoxy, C$_{1-4}$ haloalkoxy, C$_{2-4}$ alkenyl, C$_{2-4}$ alkynyl, C$_{1-4}$ alkylcarbonyl, C$_{1-4}$ alkoxycarbonyl, amino, C$_{1-4}$ alkylamino, di-C$_{1-4}$ alkylamino, and C$_{1-4}$ alkylsulfonyl; and q and r are each independently an integer selected from 0, 1, 2, 3, 4, and 5; provided that proper valencies are not exceeded.

In some embodiments, the compound of Formula II is a compound of Formula IIa:

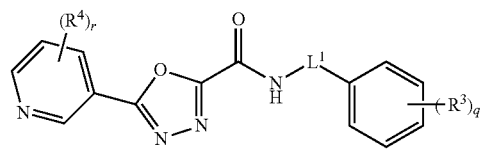

IIa or a pharmaceutically acceptable salt thereof.

In some embodiments, the compound of Formula II is a compound of Formula IIb:

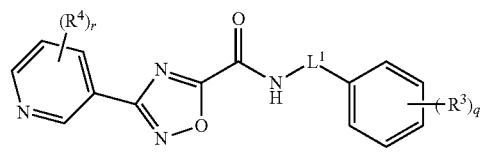

IIb or a pharmaceutically acceptable salt thereof.

In some embodiments, L$^1$ is selected from straight chain C$_{2-3}$ alkylene; which is optionally substituted by 1 or 2 methyl groups. In some embodiments, L$^1$ is selected from —CH$_2$—CH$_2$— and —CH(CH$_3$)—CH$_2$—CH$_2$—. In some embodiments, L$^1$ is —CH$_2$—CH$_2$—.

In some embodiments, r is 0. In some embodiments, q is 0, 1, or 2. In some embodiments, r is 0; and q is 0, 1, or 2.

In some embodiments, each R$^3$ is independently selected from —OR$^a$, —NR$^e$R$^f$, —NR$^c$C(O)R$^d$, halogen, C$_{1-6}$ alkyl, C$_{1-6}$ haloalkyl, C$_{2-6}$ alkynyl, C$_{6-10}$ aryl, and C$_{1-9}$ heteroaryl. In some embodiments, each R$^3$ is independently selected from —OR$^a$, halogen, C$_{1-6}$ alkyl, and C$_{6-10}$ aryl. In some embodiments, each R$^3$ is independently selected from chloro, ethyl, hydroxyl, methoxy, ethoxy, and phenyl.

In some embodiments:
each R$^a$, R$^c$, R$^d$, R$^e$, R$^f$, R$^m$, R$^o$, R$^p$, R$^r$, and R$^q$ is independently selected from H and C$_{1-6}$ alkyl; and
each R$^b$ and R$^n$ is independently selected from C$_{1-6}$ alkyl.

In some embodiments:
L$^1$ is selected from straight chain C$_{2-3}$ alkylene; which is optionally substituted by 1 or 2 methyl groups;
each R$^3$ is independently selected from —OR$^a$, —NR$^e$R$^f$, —NR$^c$C(O)R$^d$, halogen, C$_{1-6}$ alkyl, C$_{1-6}$ haloalkyl, C$_{2-6}$ alkynyl, C$_{6-10}$ aryl, and C$_{1-9}$ heteroaryl;
each R$^a$, R$^c$, R$^d$, R$^e$, and R$^f$ is independently selected from H and C$_{1-6}$ alkyl; and
each R$^b$ is independently selected from C$_{1-6}$ alkyl;
r is 0; and
q is 0, 1, or 2.

In some embodiments:
L$^1$ is selected from —CH$_2$—CH$_2$— and —CH(CH$_3$)—CH$_2$—CH$_2$—;
each R$^3$ is independently selected from —OR$^a$, halogen, C$_{1-6}$ alkyl, and C$_{6-10}$ aryl;
each R$^a$ is independently selected from H and C$_{1-4}$ alkyl;
r is 0; and
q is 0, 1, or 2.

In some embodiments:
L$^1$ is selected from —CH$_2$—CH$_2$— and —CH(CH$_3$)—CH$_2$—CH$_2$—;
each R$^3$ is independently selected from chloro, ethyl, hydroxyl, methoxy, ethoxy, and phenyl;
r is 0; and
q is 0, 1, or 2.

In some embodiments, any $R^3$ group is at the meta or para position of the phenyl ring.

In some embodiments, the compound is selected from:
N-(3,4-diethoxyphenethyl)-5-(pyridin-3-yl)-1,3,4-oxadiazole-2-carboxamide;
N-(phenethyl)-5-(pyridin-3-yl)-1,3,4-oxadiazole-2-carboxamide;
N-(3,5-dimethoxyphenethyl)-5-(pyridin-3-yl)-1,3,4-oxadiazole-2-carboxamide;
N-(4-ethylphenethyl)-5-(pyridin-3-yl)-1,3,4-oxadiazole-2-carboxamide;
N-(4-hydroxyphenethyl)-5-(pyridin-3-yl)-1,3,4-oxadiazole-2-carboxamide;
N-(3,4-dihydoxyphenethyl)-5-(pyridin-3-yl)-1,3,4-oxadiazole-2-carboxamide;
N-(4-phenylphenethyl)-5-(pyridin-3-yl)-1,3,4-oxadiazole-2-carboxamide;
N-(4-(4-methoxyphenyl)butan-2-yl)-5-(pyridin-3-yl)-1,3,4-oxadiazole-2-carboxamide;
N-(3-chlorophenethyl)-5-(pyridin-3-yl)-1,3,4-oxadiazole-2-carboxamide; and
N-(4-ethoxyphenethyl)-3-(pyridin-3-yl)-1,2,4-oxadiazole-5-carboxamide.

In still further embodiments, the agent is a compound of Formula III:

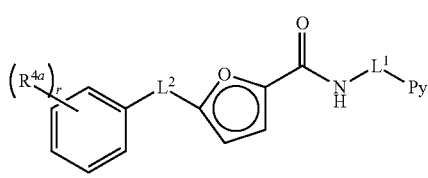

III or a pharmaceutically acceptable salt thereof; wherein:
$L^1$ is $C_{1-3}$ straight chain alkylene;
$L^2$ is $C_{1-3}$ straight chain heteroalkylene;
Py is a 6-membered heteroaryl ring, which is optionally substituted by 1, 2, 3, or 4 independently selected $R^{3a}$ groups;
each $R^{3a}$ and $R^{4a}$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy; and
r is an integer independently selected from 0, 1, 2, 3, 4, and 5.

In some embodiments, $L^1$ is —CH$_2$—.
In some embodiments, $L^2$ is straight chain $C_2$ heteroalkylene, having one sulfur or oxygen atom. In some embodiments, $L^2$ is —CH$_2$—S—CH$_2$—.

In some embodiments, Py is a pyridine ring, which is optionally substituted by 1, 2, 3, or 4 independently selected $R^{3a}$ groups. In some embodiments, Py is pyridin-3-yl, which is optionally substituted by 1, 2, 3, or 4 independently selected $R^{3a}$ groups.

In some embodiments, the compound is 5-(3-fluorobenzylthio)methyl)-N-(pyridin-3-ylmethyl)furan-2-carboxamide, or a pharmaceutically acceptable salt thereof.

In other embodiments, the agent is a compound of Formula IV:

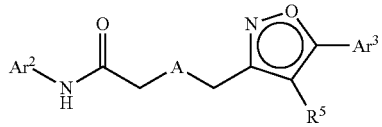

IV or a pharmaceutically acceptable salt thereof; wherein:
A is S or O;
$Ar^2$ is $C_{6-10}$ aryl or $C_{2-9}$ heteroaryl, each of which is optionally substituted by 1, 2, 3, or 4 independently selected $R^A$ groups;
$Ar^3$ is $C_{6-10}$ aryl or $C_{2-9}$ heteroaryl, each of which is optionally substituted by 1, 2, 3, or 4 independently selected $R^B$ groups;
$R^5$ is selected from independently selected from H, halogen, cyano, nitro, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl; wherein said $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl are each optionally substituted by 1, 2, 3, or 4 independently selected $R^{5'}$ groups;
each $R^A$ is independently selected from halogen, cyano, nitro, hydroxyl, carboxy, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl; wherein said $C_{1-6}$ alkylcarbonyl, $C_{1-6}$ alkoxycarbonyl, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl are each optionally substituted by 1, 2, 3, or 4 independently selected $R^{A'}$ groups;
each $R^B$ is independently selected from halogen, cyano, nitro, hydroxyl, carboxy, $C_{1-4}$ alkyl, $C_{1-4}$ haloalkyl, $C_{1-4}$ alkoxy, $C_{1-4}$ haloalkoxy, $C_{2-4}$ alkenyl, $C_{2-4}$ alkynyl, $C_{1-4}$ alkylcarbonyl, $C_{1-4}$ alkoxycarbonyl, amino, $C_{1-4}$ alkylamino, di-$C_{1-4}$ alkylamino, and $C_{1-4}$ alkylsulfonyl;
each $R^{5'}$ is independently selected from halogen, cyano, nitro, hydroxyl, carboxy, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$ alkylamino; and
each $R^{A'}$ is independently selected from halogen, cyano, nitro, hydroxyl, carboxy, $C_{1-4}$ alkyl, $C_{1-4}$ haloalkyl, $C_{1-4}$ alkoxy, $C_{1-4}$ haloalkoxy, amino, $C_{1-4}$ alkylamino, and di-$C_{1-4}$ alkylamino.

In some embodiments, the compound of Formula IV is a compound of Formula IVa:

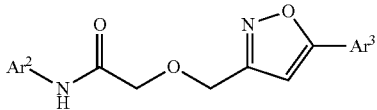

IVa or a pharmaceutically acceptable salt thereof.

In some embodiments, the compound of Formula IV is a compound of Formula IVb:

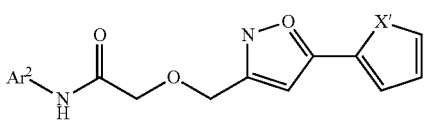

IVb or a pharmaceutically acceptable salt thereof; wherein X' is O or S.

In some embodiments, $Ar^2$ is a 6-membered heteroaryl ring, which is optionally substituted by 1, 2, 3, or 4 independently selected $R^A$ groups. In some embodiments, $Ar^2$ is a pyridine ring, which is optionally substituted by 1, 2, 3, or 4 independently selected $R^A$ groups. In some embodiments, $Ar^2$ is pyridin-3-yl, which is optionally substituted by 1, 2, or 3 independently selected $R^A$ groups.

In some embodiments, $Ar^3$ is a 5-membered heteroaryl ring, which is optionally substituted by 1, 2, or 3 independently selected $R^B$ groups. In some embodiments, $Ar^3$ is furan-2-yl, or thiophen-2-yl. In some embodiments, $Ar^3$ is furan-2-yl.

In some embodiments, $R^5$ is selected from H, halogen, hydroxyl, cyano, nitro, $C_{1-6}$ alkyl, phenyl, and $C_{1-6}$ heteroaryl. In some embodiments, $R^5$ is H.

In some embodiments, each $R^A$ is independently selected from halogen, cyano, nitro, $C_{1-6}$ alkyl, $C_{1-6}$ alkoxy, $C_{1-6}$ haloalkoxy, amino, $C_{1-6}$ alkylamino, di-$C_{1-6}$ alkylamino, phenyl, phenyl-$C_{1-3}$ alkyl, $C_{1-6}$ heteroaryl, and $C_{1-6}$ heteroaryl-$C_{1-3}$ alkyl; wherein said $C_{1-6}$ alkyl, $C_{1-6}$ alkoxy, $C_{1-6}$ haloalkoxy, amino, $C_{1-6}$ alkylamino, di-$C_{1-6}$ alkylamino, phenyl, phenyl-$C_{1-3}$ alkyl, $C_{1-6}$ heteroaryl, and $C_{1-6}$ heteroaryl-$C_{1-3}$ alkyl are each optionally substituted by 1, 2, 3, or 4 independently selected $R^{A'}$ groups. In some embodiments, each $R^A$ is selected from $C_{1-6}$ alkyl, phenyl-$C_{1-3}$ alkyl and $C_{1-6}$ heteroaryl-$C_{1-3}$ alkyl, wherein said phenyl-$C_{1-3}$ alkyl and $C_{1-6}$ heteroaryl-$C_{1-3}$ alkyl are each optionally substituted by 1, 2, 3, or 4 independently selected $R^{A'}$ groups.

In some embodiments, the compound of Formula IV is a compound of Formula IVb:

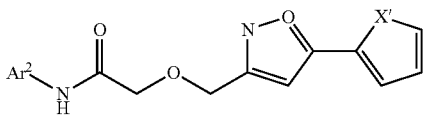

IVb or a pharmaceutically acceptable salt thereof; wherein:
X' is O or S;
$Ar^2$ is a pyridine ring, which is optionally substituted by 1, 2, or 3 $R^A$ groups;
each $R^A$ is independently selected from halogen, cyano, nitro, $C_{1-6}$ alkyl, $C_{1-6}$ alkoxy, $C_{1-6}$ haloalkoxy, amino, $C_{1-6}$ alkylamino, di-$C_{1-6}$ alkylamino, phenyl, phenyl-$C_{1-3}$ alkyl, $C_{1-6}$ heteroaryl, and $C_{1-6}$ heteroaryl-$C_{1-3}$ alkyl; wherein said $C_{1-6}$ alkyl, $C_{1-6}$ alkoxy, $C_{1-6}$ haloalkoxy, amino, $C_{1-6}$ alkylamino, di-$C_{1-6}$ alkylamino, phenyl, phenyl-$C_{1-3}$ alkyl, $C_{1-6}$ heteroaryl, and $C_{1-6}$ heteroaryl-$C_{1-3}$ alkyl are each optionally substituted by 1, 2, 3, or 4 independently selected $R^{A'}$ groups; and
each $R^{A'}$ is halogen.

In some embodiments, the compound is selected from:
2-((3-(furan-2-yl)isoxazol-5-yl)methoxy)-N-(pyridin-3-yl)acetamide, or a pharmaceutically acceptable salt thereof.

In other embodiments, the agent is a compound of Formula V:

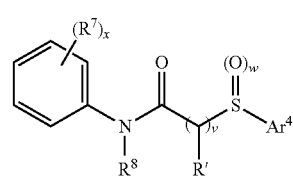

V or a pharmaceutically acceptable salt thereof; wherein:
$Ar^4$ is a 5- or 6-membered heteroaryl ring, which is optionally substituted with 1, 2, 3, 4, or 5 independently selected $R^C$ groups;
each R' is independently selected from H and $C_{1-3}$ alkyl;
each $R^7$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl; wherein said $C_{1-6}$ alkylcarbonyl, $C_{1-6}$ alkoxycarbonyl, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-7}$ cycloalkyl, $C_{3-7}$ cycloalkyl-$C_{1-3}$ alkyl, $C_{2-6}$ heterocycloalkyl, $C_{2-6}$ heterocycloalkyl-$C_{1-3}$ alkyl, phenyl, phenyl-$C_{1-3}$ alkyl, $C_{1-6}$ heteroaryl, and $C_{1-6}$ heteroaryl-$C_{1-3}$ alkyl are each optionally substituted by 1, 2, 3, or 4 independently selected $R^{7'}$ groups;
$R^8$ is selected from H and $C_{1-4}$ alkyl;
each $R^C$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-9}$ heteroaryl, and $C_{1-9}$ heteroaryl-$C_{1-3}$ alkyl; wherein said $C_{1-6}$ alkylcarbonyl, $C_{1-6}$ alkoxycarbonyl, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, $C_{3-10}$ cycloalkyl, $C_{3-10}$ cycloalkyl-$C_{1-3}$ alkyl, $C_{2-10}$ heterocycloalkyl, $C_{2-10}$ heterocycloalkyl-$C_{1-3}$ alkyl, $C_{6-10}$ aryl, $C_{6-10}$ aryl-$C_{1-3}$ alkyl, $C_{1-9}$ heteroaryl, and $C_{1-9}$ heteroaryl-$C_{1-3}$ alkyl are each optionally substituted by 1, 2, 3, or 4 independently selected $R^{C'}$ groups;
each $R^{7'}$ and $R^{C'}$ is independently selected from $C_{1-4}$ alkyl, $C_{1-4}$ haloalkyl, halogen, cyano, nitro, amino, hydroxyl, $C_{1-4}$ alkylamino, di-$C_{1-4}$ alkylamino, $C_{1-4}$ alkylsulfonyl, $C_{1-4}$ alkoxy, and $C_{1-4}$ haloalkoxy;
x is an integer selected from 0, 1, 2, 3, 4, and 5;
v is 1 or 2; and
w is 0, 1, or 2.

In some embodiments, $Ar^4$ is a 6-membered heteroaryl ring having at least one N ring member, which is optionally substituted with 1, 2, 3, 4, or 5 independently selected $R^C$ groups. In some embodiments, $Ar^4$ is a pyrimidine ring, which is optionally substituted with 1, 2, 3, 4, or 5 independently selected $R^C$ groups. In some embodiments, $Ar^4$ is pyrimidin-2-yl, which is optionally substituted with 1, 2, 3, 4, or 5 independently selected $R^C$ groups.

In some embodiments, $R^8$ is H.

In some embodiments, each R' is H.

In some embodiments, x is 0, 1, 2, or 3. In some embodiments, v is 2. In some embodiments, w is 2.

In some embodiments, each $R^7$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy. In some embodiments, each $R^7$ is independently selected from $C_{1-6}$ alkoxy, $C_{1-6}$ haloalkoxy, carboxy, $C_{1-6}$ alkylcarbonyl, $C_{1-6}$ alkoxycarbonyl, $C_{1-6}$ alkyl, and $C_{1-6}$ haloalkyl. In some embodiments, each $R^7$ is independently selected from $C_{1-6}$ haloalkoxy. In some embodiments, each $R^7$ is independently selected from trifluoromethoxy.

In some embodiments, each $R^C$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and $C_{2-10}$ heterocycloalkyl; wherein said $C_{1-6}$ alkylcarbonyl, $C_{1-6}$ alkoxycarbonyl, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, $C_{1-6}$ haloalkoxy, and $C_{2-10}$ heterocycloalkyl are each optionally substituted by 1, 2, 3, or 4 independently selected $R^{C'}$ groups. In some embodiments, each $R^C$ is independently selected from halogen, cyano, $C_{1-6}$ alkyl, $C_{1-6}$ haloalkyl, and $C_{2-10}$ heterocycloalkyl, wherein said $C_{1-6}$ alkyl, $C_{1-6}$ haloalkyl, and $C_{2-10}$ heterocycloalkyl are each optionally substituted by 1, 2, 3, or 4 independently selected $R^{C'}$ groups.

In some embodiments:
$Ar^4$ is a 6-membered heteroaryl ring having at least one N ring member, which is optionally substituted with 1, 2, 3, 4, or 5 independently selected $R^C$ groups;
each R' is H;
each $R^7$ is independently $C_{1-6}$ haloalkoxy;
$R^8$ is H;
each $R^C$ is independently selected from halogen, cyano, $C_{1-6}$ alkyl, $C_{1-6}$ haloalkyl, and $C_{2-10}$ heterocycloalkyl, wherein said $C_{1-6}$ alkyl, $C_{1-6}$ haloalkyl, and $C_{2-10}$ heterocycloalkyl are each optionally substituted by 1, 2, 3, or 4 independently selected $R^{C'}$ groups;
x is 0, 1, 2, or 3;
v is 1 or 2; and
w is 2.

In some embodiments, the compound is selected from:

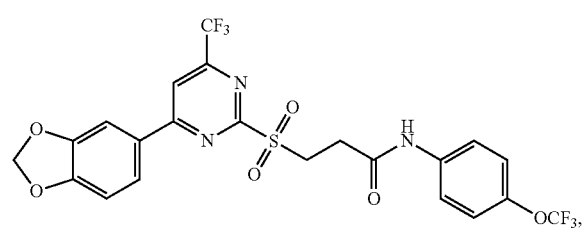 [SMILES: O=C(CCS(=O)(=O)c1nc(-c2ccc3c(c2)OCO3)cc(C(F)(F)F)n1)Nc1ccc(OC(F)(F)F)cc1]

or a pharmaceutically acceptable salt thereof.

In some embodiments, the agent is a compound of Formula VI or VII:

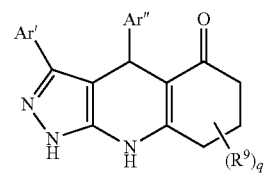

VI

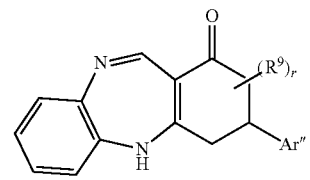

VII or a pharmaceutically acceptable salt thereof; wherein:

Ar' is $C_{6-10}$ aryl or $C_{1-9}$ heteroaryl, each of which is optionally substituted by 1, 2, 3, or 4 independently selected $R^s$ groups;

Ar'' is $C_{6-10}$ aryl or $C_{1-9}$ heteroaryl, each of which is optionally substituted by 1, 2, 3, or 4 independently selected $R^t$ groups;

each $R^9$ is independently selected from halogen, cyano, nitro, carboxy, hydroxyl, $C_{1-6}$ alkylcarbonyl, $C_{1-6}$ alkoxycarbonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

each $R^s$ and $R^t$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;

q is an integer selected from 0, 1, 2, and 3; and r is an integer selected from 0, 1, 2, 3, 4, 5, and 6.

In some embodiments, the agent is a compound of Formula VI:

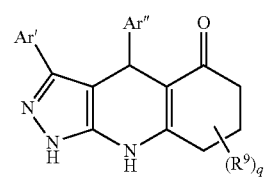

VI or a pharmaceutically acceptable salt thereof; wherein

Ar' is phenyl, which is optionally substituted by 1, 2, or 3 independently selected $R^s$ groups;

Ar'' is phenyl, which is optionally substituted by 1, 2, or 3 independently selected $R^t$ groups;

each $R^9$ is independently selected $C_{1-6}$ alkyl;

each $R^s$ and $R^t$ is independently selected from halogen, cyano, nitro, hydroxyl, amino, $C_{1-6}$ alkylamino, di-$C_{1-6}$ alkylamino, $C_{1-6}$ alkylsulfonyl, $C_{1-6}$ alkyl, $C_{1-6}$ haloalkyl, $C_{1-6}$ alkoxy, and $C_{1-6}$ haloalkoxy;

q is an integer selected from 0, 1, or 2.

In some embodiments, the agent is a compound of Formula VII:

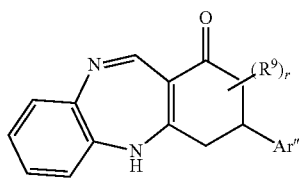

VII or a pharmaceutically acceptable salt thereof; wherein
Ar'' is phenyl, which is optionally substituted by 1, 2, or 3 independently selected $R^t$ groups;
each $R^9$ is independently selected from halogen, cyano, nitro, carboxy, hydroxyl, $C_{1-6}$ alkyl, $C_{1-6}$ haloalkyl, $C_{1-6}$ alkoxy, and $C_{1-6}$ haloalkoxy, if $R^9$ is attached to the fused phenyl ring; or
each $R^9$ is independently selected from $C_{1-6}$ alkyl, $C_{1-6}$ haloalkyl, $C_{1-6}$ alkoxy, and $C_{1-6}$ haloalkoxy, if $R^9$ is not attached to the fused phenyl ring;
each $R^t$ is independently selected from halogen, cyano, nitro, hydroxyl, amino, $C_{1-6}$ alkylamino, di-$C_{1-6}$ alkylamino, $C_{1-6}$ alkylsulfonyl, $C_{1-6}$ alkyl, $C_{1-6}$ haloalkyl, $C_{1-6}$ alkoxy, and $C_{1-6}$ haloalkoxy;
q is an integer selected from 0, 1, or 2.

In some embodiments, the compound is selected from:

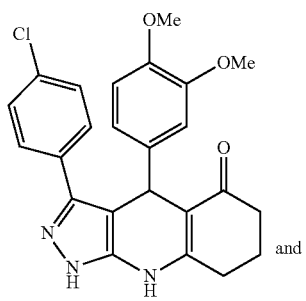

and

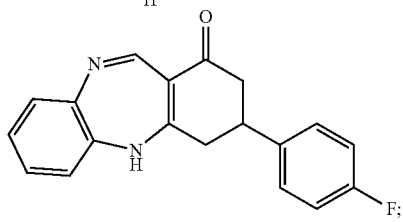

or a pharmaceutically acceptable salt thereof.

In some embodiments, the agent is a compound of Formula VIII:

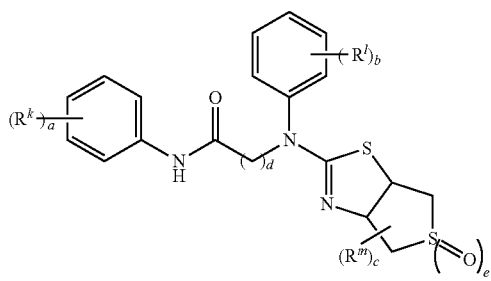

VIII or a pharmaceutically acceptable salt thereof; wherein:
each $R^k$ and $R^l$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;
each $R^m$ is independently selected from fluoro, cyano, nitro, carboxy, hydroxyl, $C_{1-6}$ alkylcarbonyl, $C_{1-6}$ alkoxycarbonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;
a and b are each independently an integer selected from 0, 1, 2, 3, 4, and 5;
c is an integer selected from 0, 1, 2, 3, and 4;
d is an integer selected from 1, 2, and 3; and
e is an integer selected from 0, 1, and 2.

In some embodiments:
each $R^k$ and $R^l$ is independently selected from halogen, cyano, nitro, carboxy, hydroxyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;
each $R^m$ is independently selected from $C_{1-6}$ alkyl;
a and b are each independently an integer selected from 0, 1, and 2;
c is an integer selected from 0, 1, and 2;
d is 1; and
e is 2.

In some embodiments, the compound is

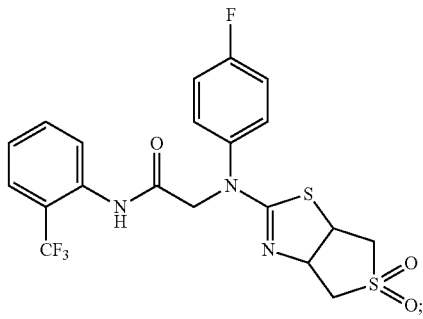 [SMILES: O=C(CN(C1=NC2CS(=O)(=O)CC2S1)c1ccc(F)cc1)Nc1ccccc1C(F)(F)F]

or a pharmaceutically acceptable salt thereof.

In some embodiments, the agent is a compound of Formula IX:

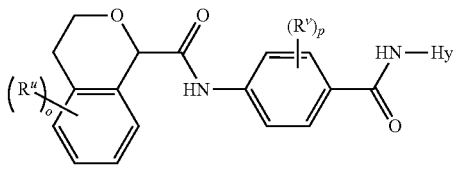

IX or a pharmaceutically acceptable salt thereof; wherein:
Hy is a 6-membered heteroaryl group, which is optionally substituted with 1, 2, 3, or 4 independently selected $R^w$ groups;
each $R^u$, $R^v$, and $R^w$ is independently selected from halogen, cyano, nitro, carboxy, hydroxyl, $C_{1-6}$ alkylcarbonyl, $C_{1-6}$ alkoxycarbonyl, amino, $C_{1-6}$ alkylamino, di-$C_{1-6}$ alkylamino, $C_{1-6}$ alkylsulfonyl, $C_{1-6}$ alkyl, $C_{2-6}$ alkenyl, $C_{2-6}$ alkynyl, $C_{1-6}$ haloalkyl, $C_{1-6}$ alkoxy, and $C_{1-6}$ haloalkoxy;
o is an integer selected from 0, 1, 2, 3, 4, 5, and 6; and
p is an integer selected from 0, 1, 2, 3, and 4.

In some embodiments, Hy is a pyridine ring, which is optionally substituted with 1, 2, 3, or 4 independently selected $R^w$ groups. In some embodiments, Hy is pyridin-3-yl, which is optionally substituted with 1, 2, 3, or 4 independently selected $R^w$ groups.

In some embodiments, the compound is

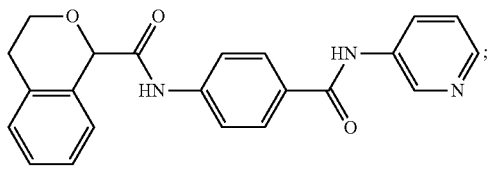 [SMILES: O=C(Nc1cccnc1)c1ccc(NC(=O)C2OCCc3ccccc32)cc1]

or a pharmaceutically acceptable salt thereof.

At various places in the present specification, substituents of compounds are disclosed in groups or in ranges. It is specifically intended that the compounds include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

For compounds in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

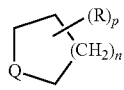

then it is understood that substituent R can occur p number of times on the ring, and R can be a different moiety at each occurrence. It is understood that each R group may replace any hydrogen atom attached to a ring atom, including one or both of the $(CH_2)_n$ hydrogen atoms. Further, in the above example, should the variable Q be defined to include hydrogens, such as when Q is the to be $CH_2$, NH, etc., any floating substituent such as R in the above example, can replace a hydrogen of the Q variable as well as a hydrogen in any other non-variable component of the ring. Unless otherwise indicated, should floating substituent R appear on a fused ring system, the substituent may replace a hydrogen atom at any ring atom in the fused ring system.

The compounds described herein can be asymmetric (e.g., having one or more stereocenters). All stereoisomers, such as enantiomers and diastereomers, are intended unless otherwise indicated. Compounds described herein that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds described herein may be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds described herein further include hydrates and solvates, as well as anhydrous and non-solvated forms. Compounds described herein can also include all isotopes of atoms occurring in the intermediates or final compounds. Isotopes include those atoms having the same atomic number but different mass numbers. For example, isotopes of hydrogen include tritium and deuterium.

The compounds can also include salt forms of the compounds described herein. Examples of salts (or salt forms) include, but are not limited to, mineral or organic acid salts of basic residues such as amines, alkali or organic salts of acidic residues such as carboxylic acids, and the like. Generally, the salt forms can be prepared by reacting the free base or acid with stoichiometric amounts or with an excess of the desired salt-forming inorganic or organic acid or base in a suitable solvent or various combinations of solvents.

The compounds also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in their entireties.

The term, "compound" as used herein is meant to include all stereoisomers, tautomers, and isotopes of the structures depicted.

As used herein, the phrase "optionally substituted" means unsubstituted or substituted. As used herein, the term "substituted" means that a hydrogen atom is removed and replaced by a substituent. It is understood that substitution at a given atom is limited by valency.

As used herein, the term "$C_{n-m}$ alkyl", employed alone or in combination with other terms, refers to a saturated hydrocarbon group that may be straight-chain or branched, having n to m carbon atoms. In some embodiments, the alkyl group contains 1 to 6, or 1 to 4 carbon atoms. Examples of alkyl moieties include, but are not limited to, chemical groups such as methyl, ethyl, n-propyl, isopropyl, n-butyl, tert-butyl, isobutyl, sec-butyl, 2-methyl-1-butyl, n-pentyl, 3-pentyl, n-hexyl, 1,2,2-trimethylpropyl, n-heptyl, n-octyl, and the like.

As used herein, the term "$C_{n-m}$ alkylene", employed alone or in combination with other terms, refers to a divalent alkyl group. In some embodiments, the alkylene group contains 1 to 8, 1 to 6, or 1 to 4 carbon atoms.

As used herein, the term "straight chain $C_{n-m}$ alkylene", employed alone or in combination with other terms, refers to an unbranched alkylene group having n to m carbon atoms. In some embodiments, the alkylene group contains 1 to 6, 1 to 4, or 1 to 3 carbon atoms.

As used herein, the term "$C_{n-m}$ alkoxy", employed alone or in combination with other terms, refers to an group of formula —O-alkyl, having n to m carbon atoms. Example alkoxy groups include methoxy, ethoxy, propoxy (e.g., n-propoxy and isopropoxy), t-butoxy, and the like.

As used herein, the term "straight chain $C_{n-m}$ heteroalkylene", employed along or in combination with other terms refers to a unbranched alkylene group having n to m carbon atoms and having 1 or 2 heteroatoms selected from O, S, and NH in the straight chain, wherein the heteroatoms are separated by the carbon atoms of the alkyl group.

As used herein, "$C_{n-m}$ alkenyl", employed alone or in combination with other terms, refers to an alkyl group having one or more double carbon-carbon bonds and n to m carbon atoms. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{n-m}$ alkynyl", employed alone or in combination with other terms, refers to an alkyl group having one or more triple carbon-carbon bonds, which may also optionally have one or more double carbon-carbon bonds, and having n to m carbon atoms. In some embodiments, the alkynyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, the term "amino", employed alone or in combination with other terms, refers to a group of formula —NH$_2$.

As used herein, the term "$C_{n-m}$ alkylamino", employed alone or in combination with other terms, refers to a group of formula —NH(alkyl), wherein the alkyl group has n to m carbon atoms. In some embodiments, the alkyl group has 1 to 6, 1 to 4, or 1 to 3 carbon atoms.

As used herein, the term "di-$C_{n-m}$ alkylamino", employed alone or in combination with other terms, refers to a group of formula —N(alkyl)$_2$, wherein each alkyl group independently has n to m carbon atoms. In some embodiments, each alkyl group has 1 to 6, 1 to 4, or 1 to 3 carbon atoms.

As used herein, the term "$C_{n-m}$ alkoxycarbonyl", employed alone or in combination with other terms, refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl", employed alone or in combination with other terms, refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl", employed alone or in combination with other terms, refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(O)— group.

As used herein, the term "carboxy", employed alone or in combination with other terms, refers to a group of formula —C(O)OH.

As used herein, the term "cyano", employed alone or in combination with other terms, refers to a group of formula —CN.

As used herein, the terms "halo" and "halogen", employed alone or in combination with other terms, refer to fluoro, chloro, bromo, and iodo. In some embodiments, halogen is fluoro.

As used herein, the term "$C_{n-m}$ haloalkyl", employed alone or in combination with other terms, refers to an alkyl group having from n to m carbon atoms and one halogen atom to 2x+1 halogen atoms which may be the same or different, where "x" is the number of carbon atoms in the alkyl group. In some embodiments, the halogen atoms are fluoro atoms. In some embodiments, the alkyl group has 1 to 6 or 1 to 4 carbon atoms. An example of a haloalkyl group is —CF$_3$.

As used herein, "$C_{n-m}$ haloalkoxy", employed alone or in combination with other terms, refers to a group of formula —O-haloalkyl, wherein the haloalkyl group has n to m carbon atoms. In some embodiments, the alkyl group has 1 to 6 or 1 to 4 carbon atoms. An example haloalkoxy group is —OCF$_3$.

As used herein, the term "$C_{n-m}$ fluoroalkyl", employed alone or in combination with other terms, refers to a $C_{n-m}$ haloalkyl wherein the halogen atoms are selected from fluorine. In some embodiments, fluorinated $C_{n-m}$ haloalkyl is fluoromethyl, difluoromethyl, or trifluoromethyl.

As used herein, the term "$C_{n-m}$ fluoroalkoxy", employed alone or in combination with other terms, refers to a $C_{n-m}$ haloalkoxy wherein the halogen atoms are selected from fluorine.

As used herein, the term "$C_{n-m}$ cycloalkyl", employed alone or in combination with other terms, refers to a non-aromatic cyclic hydrocarbon moiety, which may optionally contain one or more alkenylene or alkynylene groups as part of the ring structure, and which has n to m ring member carbon atoms. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., heteroaryl or aryl rings) fused (e.g., having a bond in common with) to the non-aromatic ring. The term "cycloalkyl" also includes bridgehead cycloalkyl groups and spirocycloalkyl groups. As used herein, "bridgehead cycloalkyl groups" refers to non-aromatic cyclic hydrocarbon moieties containing at least one bridgehead carbon, such as admantan-1-yl. As used herein, "spirocycloalkyl groups" refers to non-aromatic hydrocarbon moieties containing at least two rings fused at a single carbon atom, such as spiro[2.5]octane and the like. In some embodiments, the cycloalkyl group has 3 to 14 ring members, 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. One or more ring-forming carbon atoms of a cycloalkyl group can be oxidized to form carbonyl linkages. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, the cycloalkyl group is admanatan-1-yl.

As used herein, the term "$C_{n-m}$ cycloalkylene" refers to a divalent cycloalkyl group having n to m carbon atoms.

As used herein, the term "$C_{n-m}$ cycloalkyl-$C_{o-p}$ alkyl", employed alone or in combination with other terms, refers to a group of formula -alkylene-cycloalkyl, wherein the cycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the cycloalkyl portion has 3 to 14 ring members, 3 to 10 ring members, or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "x-membered cycloalkyl ring" refers to a monocyclic cycloalkyl ring having x ring members.

As used herein, the term "$C_{n-m}$ heterocycloalkyl", "$C_{n-m}$ heterocycloalkyl ring", or "$C_{n-m}$ heterocycloalkyl group", employed alone or in combination with other terms, refers to non-aromatic ring or ring system, which may optionally contain one or more alkenylene or alkynylene groups as part of the ring structure, which has at least one heteroatom ring member independently selected from nitrogen, sulfur and oxygen, and which has n to m ring member carbon atoms. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., heteroaryl or aryl rings) fused (e.g., having a bond in common with) to the non-aromatic ring, for example, 1,2,3,4-tetrahydroquinoline and the like. Heterocycloalkyl groups can also include bridgehead heterocycloalkyl groups and spiroheterocycloalkyl groups. As used herein, "bridgehead heterocycloalkyl group" refers to a heterocycloalkyl moiety containing at least one bridgehead atom, such as azaadmantan-1-yl and the like. As used herein, "spiroheterocycloalkyl group" refers to a heterocycloalkyl moiety containing at least two rings fused at a single atom, such as [1,4-dioxa-8-aza-spiro[4.5]decan-N-yl] and the like. In some embodiments, the heterocycloalkyl group has 3 to 20 ring-forming atoms, 3 to 10 ring-forming atoms, or about 3 to 8 ring forming atoms. The carbon atoms or hetereoatoms in the ring(s) of the heterocycloalkyl group can be oxidized to form a carbonyl, or sulfonyl group (or other oxidized linkage) or a nitrogen atom can be quaternized. In some embodiments, the heterocycloalkyl portion is a $C_{2-7}$ monocyclic heterocycloalkyl group.

As used herein, the term "x-membered heterocycloalkyl ring" refers to a monocyclic heterocycloalkyl ring having x ring members.

As used herein, the term "$C_{n-m}$ heterocycloalkyl-$C_{o-p}$ alkyl", employed alone or in combination with other terms, refers to a group of formula -alkylene-heterocycloalkyl, wherein the heterocycloalkyl portion has n to m carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heterocycloalkyl portion has 3 to 14 ring members, 3 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "$C_{n-m}$ aryl", employed alone or in combination with other terms, refers to a monocyclic or polycyclic (e.g., having 2, 3 or 4 fused rings) aromatic hydrocarbon moiety having n to m ring member carbon atoms, such as, but not limited to, phenyl, 1-naphthyl, 2-naphthyl, anthracenyl, phenanthrenyl, and the like. In some embodiments, aryl groups have from 6 to 14 carbon atoms, about 6 to 10 carbon atoms, or about 6 carbons atoms. In some embodiments, the aryl group is a monocyclic or bicyclic group.

As used herein, the term "$C_{n-m}$ aryl-$C_{o-p}$-alkyl", employed alone or in combination with other terms, refers to a group of formula -alkylene-aryl, wherein the aryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the aryl portion is phenyl. In some embodiments, the aryl group is a monocyclic or bicyclic group. In some embodiments, the arylalkyl group is benzyl.

As used herein, the term "$C_{n-m}$ heteroaryl", "$C_{n-m}$ heteroaryl ring", or "$C_{n-m}$ heteroaryl group", employed alone or in combination with other terms, refers to a monocyclic or polycyclic (e.g., having 2, 3 or 4 fused rings) aromatic hydrocarbon moiety, having one or more heteroatom ring members independently selected from nitrogen, sulfur and oxygen and having n to m ring member carbon atoms. In some embodiments, the heteroaryl group is a monocyclic or bicyclic group having 1, 2, 3, or 4 hetereoatoms independently selected from nitrogen, sulfur and oxygen. Example heteroaryl groups include, but are not limited to, pyrrolyl, azolyl, oxazolyl, thiazolyl, imidazolyl, furyl, thienyl, quinolinyl, isoquinolinyl, indolyl, benzothienyl, benzofuranyl, benzisoxazolyl, imidazo[1,2-b]thiazolyl or the like. The carbon atoms or hetereoatoms in the ring(s) of the heteroaryl group can be oxidized to form a carbonyl group, nitrogen atom can be quaternized, provided the aromatic nature of the ring is preserved for at least one ring of the heteroaryl moiety. In some embodiments, the heteroaryl group has 5 to 10 carbon atoms.

As used herein, the term "x-membered heteroaryl ring" refers to a monocyclic heteroaryl ring having x ring members.

As used herein, the term "$C_{n-m}$ heteroaryl-$C_{o-p}$-alkyl", employed alone or in combination with other terms, refers to a group of formula -alkylene-heteroaryl, wherein the heteroaryl portion has n to m ring member carbon atoms and the alkylene portion has o to p carbon atoms. In some embodiments, the alkylene portion has 1 to 4, 1 to 3, 1 to 2, or 1 carbon atom(s). In some embodiments, the alkylene portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

As used herein, the term "oxo" refers to a group of formula "=O".

As used herein, wherein a ring is indicated as, e.g., "a thiazole ring", "a pyridine ring", "a pyridimine ring", etc., the ring can be attached at any position of the ring, provided that the valency of the atom at the point of attachment is not exceeded. By contrast, in some embodiments, the exact point of attachment is clearly indicated in the name (e.g., "thiazol-2-yl", "pyridin-2-yl", "pyridin-3-yl", "pyridin-4-yl", "pyridimin-2-yl" and "pyrimidin-4-yl"). For example, the point of attachment for "thiazol-2-yl" is the 2-position of the ring.

The term "protecting group" includes, but are not limited to, the protecting groups described in Greene, et al., Protective Groups in Organic Synthesis, 4d. Ed., Wiley & Sons, 2007, which is incorporated herein by reference in its entirety.

Unless otherwise indicated herein, the point of attachment of a substituent is generally in the last portion of the name (e.g., arylalkyl is attached through the alkylene portion of the group).

Pharmaceutical Compositions

The agents described herein can be incorporated into pharmaceutical compositions. Such compositions typically include the agent and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, inhalation, transdermal (topical), transmucosal, or rectal; or oral. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL™, or corn starch; a lubricant such as magnesium stearate or STEROTES™; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa, butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models, e.g., of inflammation or disorders involving undesirable inflammation, to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography, generally of a labeled agent. Animal models useful in studies, e.g., preclinical protocols, are known in the art, for example, animal models for inflammatory disorders such as those described in Sonderstrup (2003, Springer Sem. Immunopathol., 25:35-45) and Nikula et al. (2000, Inhal Toxicol., 12 Suppl. 4:123-53), and those known in the art, e.g., for fungal infection, sepsis, cytomegalovirus infection, tuberculosis, leprosy, viral hepatitis, and infection (e.g., by mycobacteria).

In some embodiments, a therapeutically effective amount ranges from about 0.001 to 30 mg/kg body weight, for example, about 0.01 to 25 mg/kg body weight, about 0.1 to 20 mg/kg body weight, or about 1 to 10 mg/kg, 2 to 9 mg/kg, 3 to 8 mg/kg, 4 to 7 mg/kg, or 5 to 6 mg/kg body weight. The agent can be administered one or several times per day or per week for between about 1 to 10 weeks, for example, between 2 to 8 weeks, between about 3 to 7 weeks, or about 4, 5, or 6 weeks. In some instances the dosage may be required over several months or more. The skilled artisan will appreciate that certain factors may influence the dosage and timing required to effectively treat a subject, including, but not limited to the severity of the disease or disorder, previous treatments, the general health and/or age of the subject, and other diseases present. Moreover, treatment of a subject with a therapeutically effective amount of an agent such as a protein or polypeptide (including an antibody) can include a single treatment or, preferably, can include a series of treatments.

In some embodiments, the compositions comprise milligram or microgram amounts of the agent per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of the agent depend upon the potency of the agent with respect to the expression or activity to be modulated. When one or more of these agents is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

Compounds as described herein may be used for the preparation of a medicament for use in any of the methods of treatment described herein.

The compounds described herein are available commercially or from screening libraries, or can be prepared in a variety of ways known to one skilled in the art of organic synthesis. For example, certain compounds were part of the The National Screening Laboratory for the Regional Centers of Excellence in Biodefense and Emerging Infectious Diseases. Other commercial sources include ChemDiv, ChemBridge, Aurora, Tim Tec, and Scientific exchange product list. In some embodiments, compounds of Formula I may be synthesized by methods analogous to those in WO 2008/109154, which is incorporated herein by reference in its entirety (for example, see Scheme I, II, and III and related examples).

The compounds may be conveniently prepared by employing standard synthetic methods and procedures known to those skilled in the art from commercially available starting materials, compounds known in the literature, or readily prepared intermediates. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures. Those skilled in the art of organic synthesis will recognize that the nature and order of the synthetic steps presented may be varied for the purpose of optimizing the formation of the compounds of the invention.

The processes can be monitored according to any suitable method known in the art. For example, product formation can be monitored by spectroscopic means, such as nuclear magnetic resonance spectroscopy (e.g., $^1$H or $^{13}$C NMR) infrared spectroscopy, spectrophotometry (e.g., UV-visible), or mass spectrometry, or by chromatography such as high performance liquid chromatography (HPLC) or thin layer chromatography.

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., Protective Groups in Organic Synthesis, 4d. Ed., Wiley & Sons, 2007, which is incorporated herein by reference in its entirety. Adjustments to the protecting groups and formation and cleavage methods may be adjusted as necessary in light of the various substituents.

The reactions can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Suitable solvents can include halogenated solvents such as carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, 2-chloropropane, α,α,α-trifluorotoluene, 1,2-dichloroethane, 1,2-dibromoethane, hexafluorobenzene, 1,2,4-trichlorobenzene, 1,2-dichlorobenzene, chlorobenzene, fluorobenzene, mixtures thereof and the like.

Suitable ether solvents include: dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, mixtures thereof and the like.

Suitable protic solvents can include, by way of example and without limitation, water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol.

Suitable aprotic solvents can include, by way of example and without limitation, tetrahydrofuran (THF), N,N-dimethylformamide (DMF), N,N-dimethylacetamide (DMA), 1,3-dimethyl-3,4,5,6-tetrahydro-2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, ethyl formate, methyl acetate, hexachloroacetone, acetone, ethyl methyl ketone, ethyl acetate, sulfolane, N,N-dimethylpropionamide, tetramethylurea, nitromethane, nitrobenzene, or hexamethylphosphoramide.

Suitable hydrocarbon solvents include benzene, cyclohexane, pentane, hexane, toluene, cycloheptane, methylcyclohexane, heptane, ethylbenzene, m-, o-, or p-xylene, octane, indane, nonane, or naphthalene.

Supercritical carbon dioxide and ionic liquids can also be used as solvents.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes can be carried out in air or under an inert atmosphere. Typically, reactions containing reagents or products that are substantially reactive with air can be carried out using air-sensitive synthetic techniques that are well known to the skilled artisan.

In some embodiments, preparation of compounds can involve the addition of acids or bases to effect, for example, catalysis of a desired reaction or formation of salt forms such as acid addition salts.

Example acids can be inorganic or organic acids. Inorganic acids include hydrochloric acid, hydrobromic acid, sulfuric acid, phosphoric acid, and nitric acid. Organic acids include formic acid, acetic acid, propionic acid, butanoic acid, benzoic acid, 4-nitrobenzoic acid, methanesulfonic acid, p-toluenesulfonic acid, benzenesulfonic acid, tartaric acid, trifluoroacetic acid, propiolic acid, butyric acid, 2-butynoic acid, vinyl acetic acid, pentanoic acid, hexanoic acid, heptanoic acid, octanoic acid, nonanoic acid and decanoic acid.

Example bases include lithium hydroxide, sodium hydroxide, potassium hydroxide, lithium carbonate, sodium carbonate, and potassium carbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include sodium and potassium salts of methyl, ethyl, n-propyl, i-propyl, n-butyl, t-butyl, trimethylsilyl and cyclohexyl substituted amides.

Upon carrying out preparation of compounds according to the processes described herein, the usual isolation and purification operations such as concentration, filtration, extraction, solid-phase extraction, recrystallization, chromatography, and the like may be used, to isolate the desired products.

In some embodiments, the compounds can be substantially isolated. By "substantially isolated" is meant that the compound is at least partially or substantially separated from the environment in which it was formed or detected. Partial separation can include, for example, a composition enriched in the compound or intermediate, or salt thereof. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

As used herein, the expressions, "ambient temperature" and "room temperature," as used herein, are understood in the art, and refer generally to a temperature, e.g. a reaction temperature, that is about the temperature of the room in which the reaction is carried out, for example, a temperature from about 20° C. to about 30° C.

As used herein, the term "reacting" is used as known in the art and generally refers to the bringing together of chemical reagents in such a manner so as to allow their interaction at the molecular level to achieve a chemical or physical transformation. In some embodiments, the reacting involves two reagents, wherein one or more equivalents of second reagent are used with respect to the first reagent. The reacting steps of the processes described herein can be conducted for a time and under conditions suitable for preparing the identified product.

EXAMPLES

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

Example 1

Establishment of a HEK293 Cell Line Stably Expressing TLR2, CD14, and NF-κB-driven Luciferase Previous studies have shown LCMV infection induced NF-κB activation and cytokine and chemokine releasing through a TLR2 and CD14-dependent signaling pathway. Zhou S, et al., "MyD88 is critical for the development of innate and adaptive immunity during acute lymphocytic choriomeningitis virus infection." *Eur. J. Immunol.* 2005, 35(3):822-30; and Zhou, S., et al., "Lymphocytic Choriomeningitis Virus (LCMV) infection of CNS glial cells results in TLR2-MyD88/Mal-dependent inflammatory responses", *J. Neuroimmunology,* 2008,194:70-82. Luciferase is a commonly used reporter because of the high sensitivity of detection and the absence of endogenous luciferase activity in mammalian cells, thus is suitable for screening larger number of compounds. HEK293 cells (CRL-1573; ATCC) stably expressing TLR2 (HEK293-TLR2) were maintained in Dulbecco's modified Eagle medium supplemented with 10% heat-inactivated fetal bovine serum (hyClone), 100 U/ml penicillin, and 100 µg/ml streptomycin (DMEM-10% FCS). To establish an HEK293 cell line stably expressing TLR2, CD14, and NF-κB-driven firefly luciferase, HEK293-TLR2 cells were plated to 24-well plates at $1\times10^5$/well and co-transfected 24 hours later with plasmids expressing CD14-hygromycin and NF-κB-driven firefly luciferase using GeneJuice transfection reagent (Novagen) according to manufacturer's instructions. 48 hours post-transfection, cells were treated with hygromycin (200 µg/ml). After every 3 days of culture, medium was replaced with fresh culture medium containing 200 µg/ml hygromycin. After 3-4 weeks of culture in the presence of hygromycin, individual clones were then picked up and plated to new wells of 24-well tissue culture plates. During the expansion of individual clones, the concentration of hygromycin was reduced to 100 µg/ml. The expression of TLR2 and CD14 was characterized using flow cytometry staining with anti-human TLR2 (11G7 clone) and anti-human CD14 (Sigma), respectively. The cell line of HEK cells stably expressing the genes described herein was deposited at the American Type Culture Collection (ATCC), 10801 University Blvd., Manassas, Va., 20110-2209, on Oct. 1, 2009 (ATCC Accession No. PTA-10373). The cell line is further described in U.S. Prov. Appl. No. 61/262,223, entitled "Cell Line and Methods for Identifying NF-Kappa B Modulators", filed on Nov. 18, 2009, which is incorporated herein by reference in its entirety.

The functionality of these cell lines was characterized following a routine protocol. Briefly, for initial characterization, cells were seeded into 24-well plates at $1\times10^5$ cells/well and allowed to grow for 20 hours to about 70% confluence. Cells were then incubated with no stimulus (medium only) or with live LCMV-Arm. Control stimulants included $Pam_2CSK_4$ (TLR2 and TLR6 ligand; EMC Micro collection, Tuebingen, Germany) and recombinant human TNF-α (non-TLR ligand), as well as uninfected BHK-21 cell supernatant. The cultures were incubated for 16-20 hours at 37° C. in 5% $CO_2$ humidified incubator, cell lysates were prepared using Passive Lysis Buffer (Promega), and firefly luciferase activity (indicator of NF-κB activity) was measured using Steady-Glo™ Luciferase Assay System (Promega) according to the manufacturer's instructions. One of the best clones was designated SZ10, which is a representative from 12 individual clones. SZ10 cells highly expressed both TLR2 and CD14 (FIG. 1A, 1B), and responded to LCMV challenge, as well as to $Pam_2CSK_4$ (TLR2 ligand) and TNF-α (TLR independent stimuli) stimulation (FIG. 1C). Thus an HEK cell line stably expressing TLR2, CD14, and NF-κB-driven firefly luciferase was established.

Example 2

Pilot Screening to Validate SZ10 Cells with Known Activity Compounds

Figure 4:
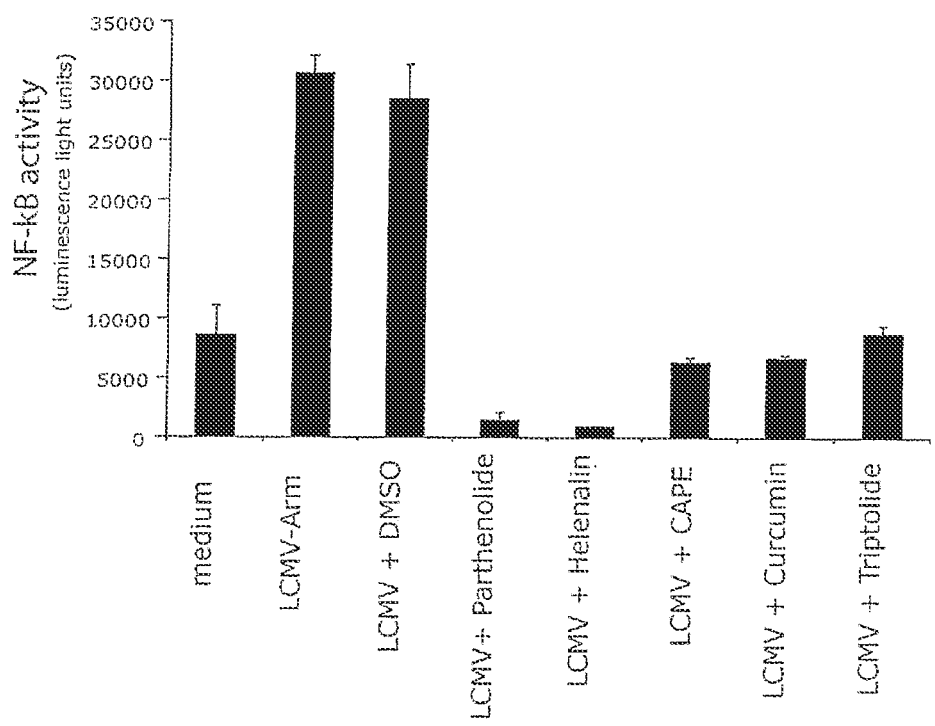
FIG. 4 depicts NF-κB activity (luminescence) determined by luciferase assay after SZ10 cells were treated with known bioactive compounds.
Figure 5:
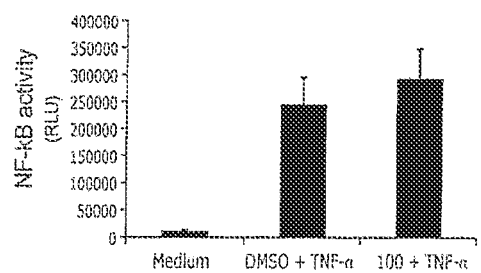
FIG. 5 depicts NF-κB activity determined by luciferase assay after treating with compound 100 or DMSO carrier and in primary screening test with SZ10 cells (FIG. 5A, 5C) and cherry picked compound 100 (FIG. 5B, 5D) following challenge with either TNF-α (FIG. 5A, 5B) or LCMV (5C, 5D).
Figure 5:
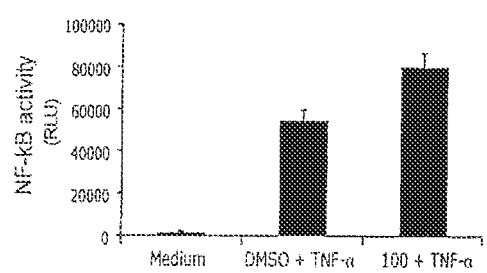
Figure 5:
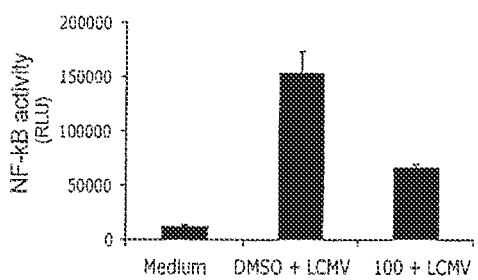
Figure 5:
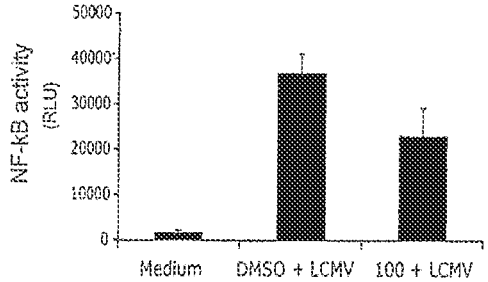

To validate the specificity and sensitivity of SZ10 cells, a pilot screening was performed with a collection of known bioactives. The collection includes many classes of compounds such as kinase inhibitors, protease inhibitors, and ion channel blockers. The screening was carried out as detailed supra in Example 3, except for modifications described herein. Accordingly, SZ10 cells were plated into 384-well plates (duplicate plates) and incubated overnight at 37° C., 5% $CO_2$. Cells were treated with "known bioactives" compounds or DMSO and incubated for 60 min. Cells were challenged with LCMV-Arm and incubated for additional 5-18 hr at 37° C., 5% $CO_2$. NF-κB activity (luminescence light unit) was determined by luciferase assay. As expected, compared with DMSO (compound carrier), all 5 known NF-κB inhibitory compounds, including known inhibitors for IκB (Parthenolide) and NF-κB (Helenalin, CAPE, Curcumin, Triptolide), effectively blocked LCMV-induced NF-κB activation (FIG. 4). Therefore, these results demonstrate that SZ10 cells and the screen protocol are suitable for screening compounds targeting LCMV-induced NF-κB activation.

Example 3

Protocol for Primary Screening of Compounds

Figure 2:
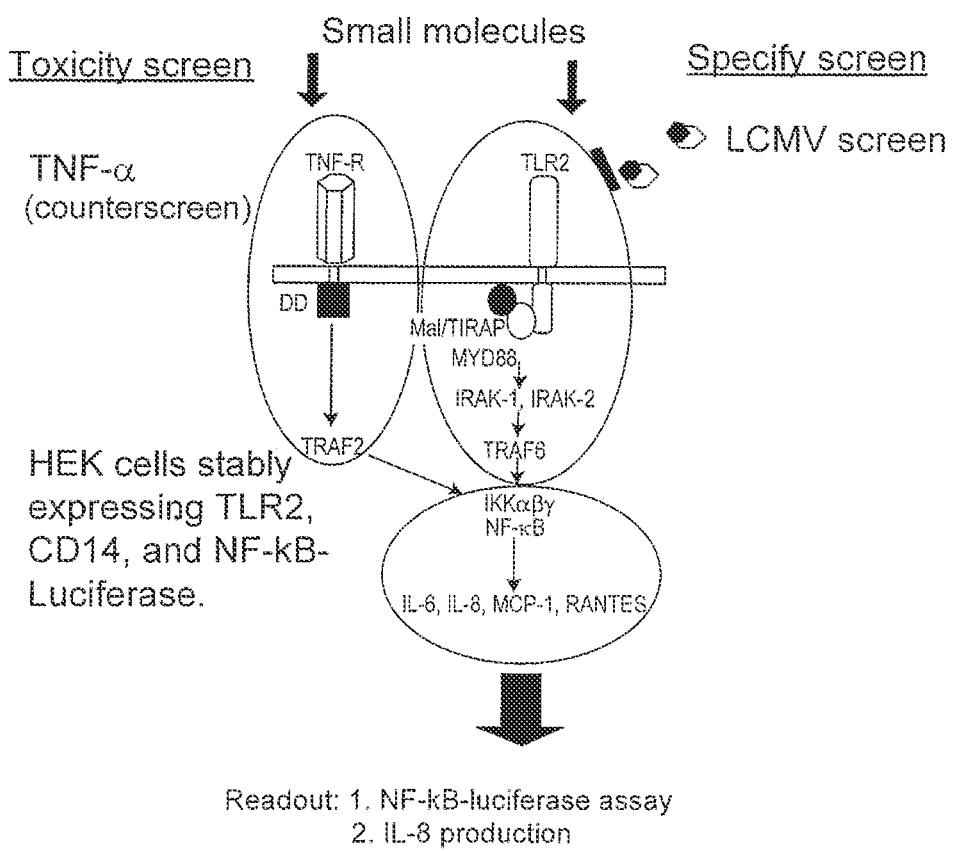
FIG. 2 depicts a working model for screening anti-LCMV-mediated inflammatory compounds.
Figure 3:
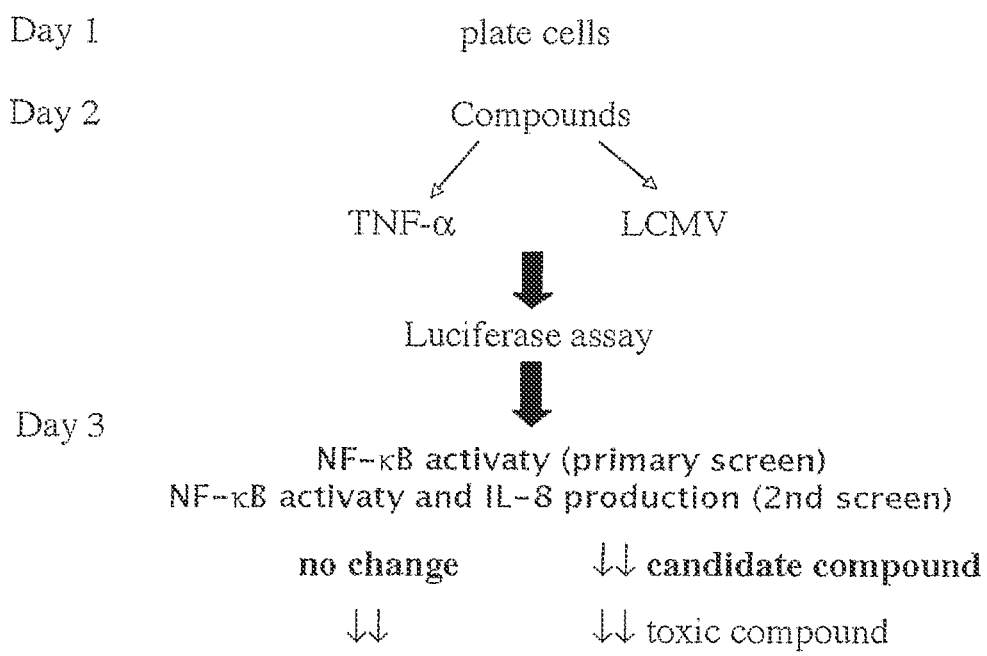
FIG. 3 depicts a schematic for screening of compounds.

Having established the reliability and suitability of the SZ10 cell line for screening compound libraries (see Example 2), we established a working model for a screen that would select for compounds that blocked NFkB activation by LCMV but would not affect activation by TNF-α (FIG. 2), of which an exemplary protocol is depicted in FIG. 3. Primary screening of small molecule compounds was carried out at the ICCB facility at Harvard University and 384-well plate format screening assay was employed throughout the primary screening. To develop the screening protocol, SZ10 cells were seeded into duplicated 384-well tissue culture white styrene plates (Corning) at 0.5-1×10³ cells/30 µl/well and incubated overnight at 37° C. in 5% $CO_2$ humidified incubator. The next day, cells were treated with compounds at 0.1 µl/well (5 mg/ml in DMSO) through an automated pin-based compound transfer robot. After incubation for 1 h at 37° C. in 5% $CO_2$ humidified incubator, cells were then challenged with either LCMV-Arm (kindly provided by Dr. Liisa K. Selin (University of Massachusetts, Medical School, MA); Brehm M A, et al., "T cell immunodominance and maintenance of memory regulated by unexpectedly cross-reactive pathogens", *Nat, Immunol.* 2002 July; 3(7):627-34) or control TNF-α for countersreen (10 µl/well) using liquid handling robot. Plates were briefly spun and cells were incubated additional 16-18 h. This protocol has been followed for the entire primary screening and secondary (cherry pick) screening. Thereafter, 20 µl/well of 1:1 pre-diluted/DPBS buffered Steady-Glo luciferase buffer were added and luciferase activity was read using Envision II plate reader. Results were recorded as luminescence.

Because TNF-α and TLR2 agonist (e.g. LCMV) utilize different adaptors to engage the innate immune signaling pathway, but both lead to activation of the common downstream transcriptional factor NF-κB targets, TNF-α was run side-by-side each time on separate plates in our full screen. Only those compounds that significantly reduced LCMV-induced NF-κB luciferase activity by 50% or greater than positive controls (DMSO only), with no change of TNF-α-induced NF-κB luciferase activity were cherry-picked for secondary screening.

For primary screening, compounds were reconstituted with dimethyl sulfoxide (DMSO) to 5-mg/ml stocks. Compound libraries screened included those from ChemDiv, Maybridge, ChemBridge, Biomol-TimTec, and some Fungal Extracts.

Example 4

Primary Screening for Small Molecule Compounds that Inhibit LCMV-induced TLR2-mediated Signaling Pathway In the primary screening, 101,306 compounds were screened according to the protocol in Example 3. 217 compounds were selected for further evaluation. These positive hits were defined as those that inhibit LCMV-induced NF-κB activity by 50% of the untreated or DMSO treated cells but challenged with LCMV. A counterscreen with TNF-α stimulation was included in each of the screening to distinguish which compounds that have a specific effect on LCMV stimulation. From the 217 hits, 10 compounds were identified (see Table 1; compounds 100, 119, 120, 121, 122, 125, 132, 133, 134, and 135) that could specifically inhibit LCMV-induced NF-κB activity and cytokine response (example in FIGS. 5A-5D). One of the 10 candidates, compound 100, was further characterized. Compound 100 was chemically pure based on HPLC/MS/MS analysis. HPLC-MS/MS was performed in the UMMS Proteomic & Mass Spectrometry Core Facility on a Thermo Scientific LTQ Surveyor quadrupole ion trap mass spectrometry system. HPLC was performed using a BetaBasic-18 reversed phase column (1×150 mm, 3 µm particle, 150 A pore size; Keystone Scientific) with gradient or isocratic elution at 50 µl/min as specified in the table. The mobile phases contained ACN in 0.1% formic acid in HPLC grade water. The column effluent was directed to the electrospray ion source of the mass spectrometer with the source at 5 kV and 275° C., the capillary and tube lens were at 25 V and 75 V respectively in the positive ion mode of operation. Product ion scans were acquired during the elution time window.

Example 4A

Compound 100 Downregulates TLR2 Expression

Figure 14:
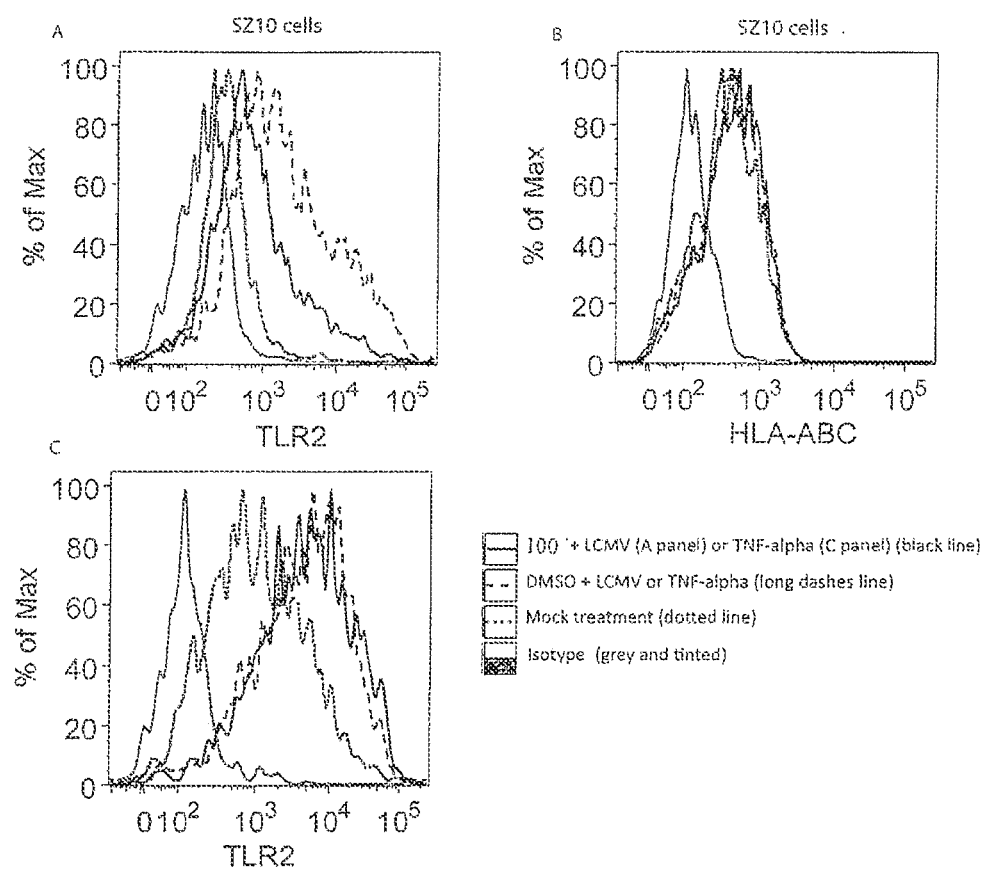
FIG. 14 depicts inhibition of LCMV-induced TLR2 expression in HEK293 cells by compound 100.

It was previously demonstrated that expression of TLR2 is required for the LCMV-induced cytokine response (Zhou, et al., J Neuroimmunol 194(1-2), 70-82 (2008); Zhou, et al., Eur J Immunol 35(3), 822-30 (2005). To further define the mechanism by which compound 100 inhibits LCMV-induced cytokine response, we examined if compound 100 affects TLR2 expression. SZ10 cells were treated with various doses of compound 100 or DMSO followed by challenge with LCMV or control TNF-α. The expression of TLR2 was examined by flow cytometry staining. The expression of HLA-ABC was utilized as a control. Accordingly, SZ10 cells were plated in 24-well plate and were mock-treated (dotted line), or treated with compound 100 (3.3 µM) (black line), or DMSO (long dashes line) for one hour followed by challenge with LCMV (FIG. 14A) or TNF-α (FIG. 14B) in the presence of compound 100 or DMSO. Twenty hours post-infection, the expression of TLR2 in SZ10 cells was determined by flow cytometry staining with anti-TLR2 antibody (clone 11G7) (FIG. 14A). The grey and tinted area represents the isotype for anti-TLR2 antibody. The expression of HLA-ABC in the same treated SZ10 cells was determined by flow cytometry staining with antibody against human HLA-ABC (FIG. 14B). Grey and tinted area, isotype control; dotted line, mock-treated cells; black line, compound 100-treated cells; lone dashes line, DMSO-treated cells. The MFI data for FIG. 14A (which shows the effect of the compound on TLR2 expression) are: isotype: 174; basal TLR2<dotted line>: 353; DMSO+LCMV<long dashes line>: 1978; compound 100+LCMV<black line>: 804. The MFI for FIG. 14C (TNF-α control for FIG. 14A) are: isotype: 132; basal TLR2<dotted line>: 1077; DMSO+TNF-α<long dashes line>: 4224; compound 100+TNF-α<black line>: 4711. LCMV challenge enhanced expression of TLR2 and DMSO did not affect LCMV induced up-expression of TLR2 (FIG. 14A. long dashes line). In contrast, incubation with compound 100 prevented LCMV-induced enhanced expression of TLR2 (FIG. 14A. black line), but did not affect the expression of HLA-ABC (FIG. 14B). Treatment with compound 100 did not affect TNF-α-induced expression of TLR2 (FIG. 14C).

Example 5

Figure 6:
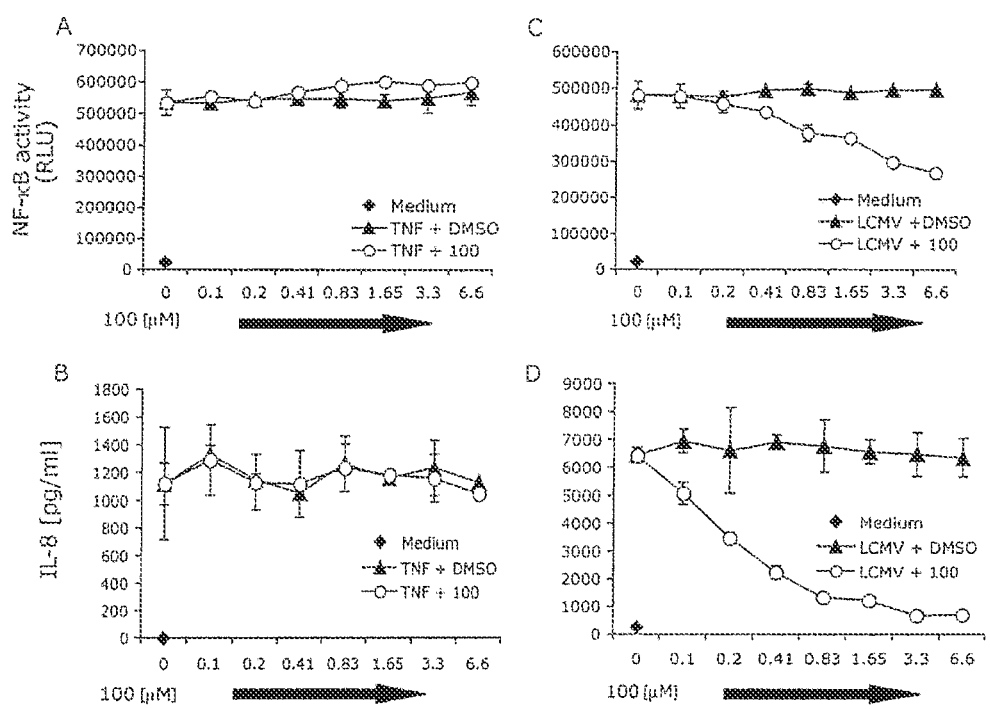
FIG. 6 depicts NF-κB activity determined by luciferase assay after treating with compound 100 or DMSO carrier at various concentrations and challenge with LCMV-Arm (C and D) or control stimulant TNF-α (A and B).

Compound 100 Inhibition of LCMV-induced NF-κB Activity and IL-8 Production in a Dose-Dependent Manner To further characterize compound 100, the effect of compound 100 on LCMV-induced NF-κB activity as well as IL-8 production was compared. HEK cells predominantly produce IL-8 and its induction is NF-κB-dependent. Accordingly, SZ10 cells were plated into 96-well plates and incubated overnight at 37° C., 5% CO2. Cells were treated with compound 100 or compound carrier DMSO at various concentrations and incubated for 60 min, then cells were challenged with either LCMV-Arm (FIGS. 6C and 6D) or control stimulant TNF-α (FIGS. 6A and B). Cells were incubated for additional 16-18 hr at 37° C., 5% $CO_2$. Levels of IL-8 (FIGS. 6B and 6D) in the culture supernatants were measured by ELISA. Cell lysates were used to determine NF-κB activity (luciferase assay) (FIGS. 6A and 6C). Data are means and standard errors of triplicate wells. Results are representative of more than five separate experiments.

Consistent with the results from primary screening and cherry-pick, compound 100 dramatically inhibited LCMV-induced NF-κB activity (FIG. 6C) and IL-8 production (FIG. 6D) in a dose-dependent manner. In contrast, compound 100 did not affect TNF-α-induced NF-κB activity (FIG. 6A) and IL-8 production (FIG. 6B). Together, these results demonstrate that compound 100 specifically blocks the LCMV-induced TLR2-dependent cytokine response.

Example 6

Compound 100 Prevents LCMV Mediated Upregulation of TLR2 Expression in SZ10 Cells It has been previously demonstrated that TLR2 is required for LCMV-induced cytokine response (Zhou S., et al., "MyD88 is critical for the development of innate and adaptive immunity during acute lymphocytic choriomeningitis virus infection" *Eur. J. Immunol.* 2005; 35(3):822-30; and Zhou S., et al., "Lymphocytic Choriomeningitis Virus (LCMV) infection of CNS glial cells results in TLR2-MyD88/Mal-dependent inflammatory responses", *J. Neuroimmunology*, 2008, 194:70-82). To further define the mechanism by which compound 100 inhibits LCMV-induced cytokine response, the effect of compound 100 on TLR2 expression was examined. SZ10 cells were treated with different doses of compound 100 or DMSO control followed by LCMV challenge as described in Example 10. The expression of TLR2 was examined by flow cytometry staining Expression of HLA-ABC was utilized as control. As expected, DMSO did not affect both TNF-α and LCMV induced up-expression of TLR2 (FIG. 8A). In contrast, compound 100 specifically prevented the LCMV-mediated enhancement of TLR2 expression (FIG. 8B). Expression of HLA-ABC was not affected by compound 100 treatment (FIG. 8C).

Example 7

Compound 100 Inhibits LCMV Replication in SZ10 and Vero Cells

To further determine whether the effect of compound 100 on LCMV induced NF-κB activity is due to block LCMV replication, both SZ10 and Vero cells were utilized, because Vero cells are sensitive to LCMV infection and are commonly used to titrate LCMV. Two quantitative methods were utilized to determine the effect of compound on LCMV replication. Accordingly, Vero cells were plated to either 24-well (to determine the expression of LCMV-NP using the flow cytometric assay) or 6-well plates (to determine the replication of LCMV using the classical plaque assay) as described in Example 11 below.

Figure 9:
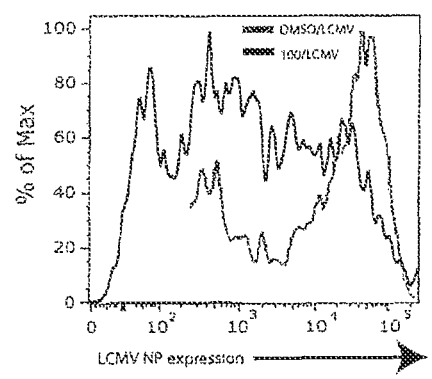
FIG. 9 depicts LCMV replication in SZ10 cells and Vero cells treated with compound 100 or DMSO carrier evaluated by either flow cytometry staining (FIG. 9A, 9B) or classic plaque assay (FIG. 9C).
Figure 9:
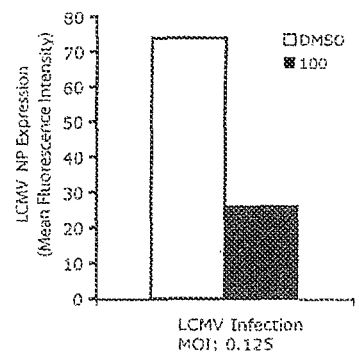
Figure 9:
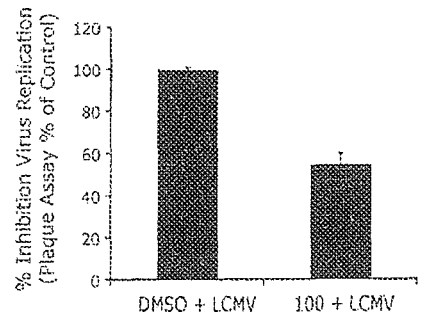

The expression of LCMV-NP was determined using an immune focus assay (FIG. 9A). To assess LCMV protein production, SZ10 cells or Vero cells were treated with compound or DMSO followed by challenge with LCMV-Arm. After adsorption for 1 h at 37° C. in 5% $CO_2$ humidified incubator, virus was removed and replaced with fresh medium. Cells were incubated for 16-18 h. LCMV replication was determined by flow cytometry intracellular staining using anti-LCMV-NP antibody VL4. Samples were acquired on a BD-LSR-II flow cytometer (Becton Dickinson). Data was analyzed with Flowjo software (Tree Star Inc.). Expression of LCMV NP in Vero cells was quantitated by means fluoresennce index (FIG. 9B) The replication of LCMV was determined using the classical plaque assay as described in Example 11 below. The effect of compound and its analogs on LCMV replication was determined using the classical plaque assay as described in Example 11 below. Results were shown as plaque reduction (FIG. 9C). Compound 100 significantly inhibited LCMV replication in SZ10 and Vero cells evaluated by either flow cytometry staining (FIGS. 9A and 9B) or classic plaque assay (FIG. 9C).

Example 7A

Effect of Analogs of Compound 100 on LCMV Replication in Vero Cells

Figure 10:
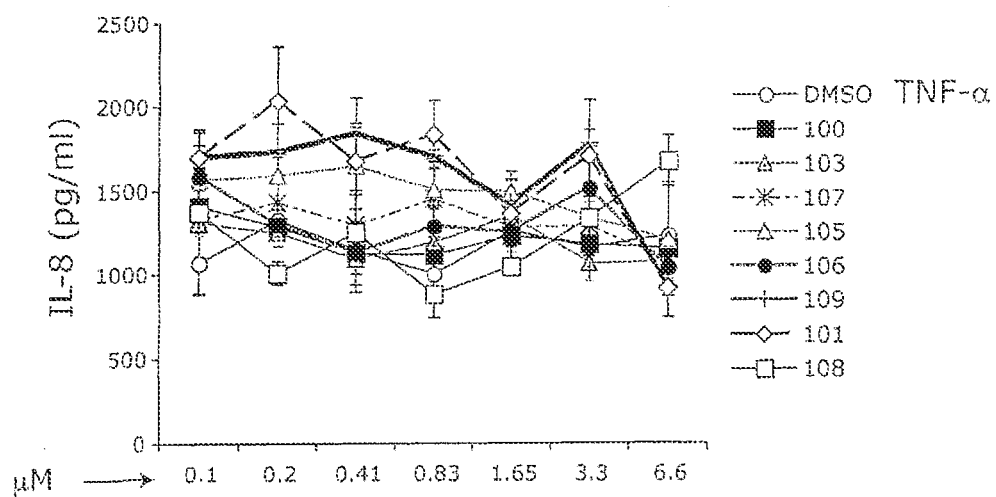
FIG. 10 depicts LCMV induced IL-8 production (FIGS. 10A, 10B) and LCMV replication (FIG. 10C) for compound 100 analogs.
Figure 10:
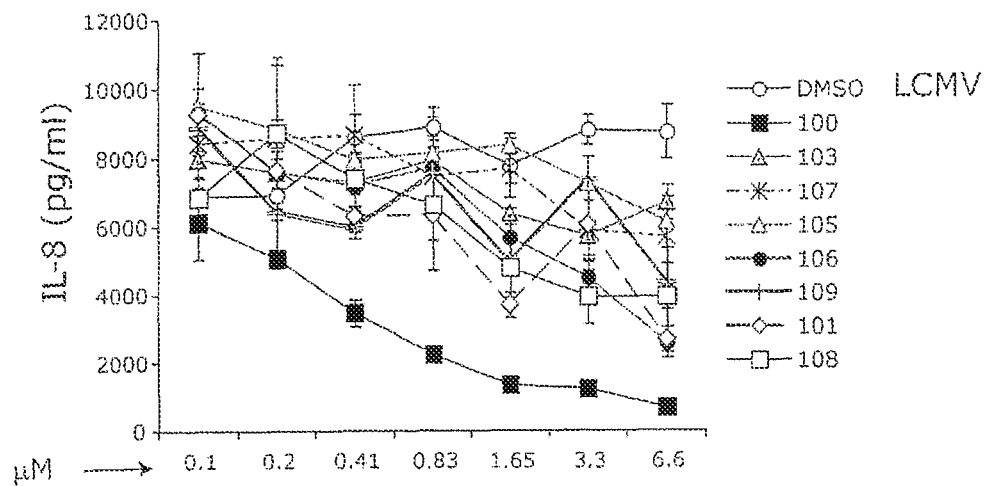

Analogs of compound 100 were evaluated as follows. SZ10 cells were plated in 96-well plates. After incubated overnight, the cells were treated with analogs of compound 100 (compounds 101 and 103-109) for 60 min followed by challenge with TNF-α (FIG. 10A) or LCMV (FIG. 10B) and IL-8 was measured by ELISA. Vero cells were plated in 6-well plates. After incubated overnight, cells were treated with compound 100 or its analogs for 60 min followed by challenge with LCMV-Arm as described in Example 11. Four days post-infection, plaques were counted and the reduction of plaques was calculated. Results were shown as fold of plaque reduction (FIG. 10C).

Figure 10C:
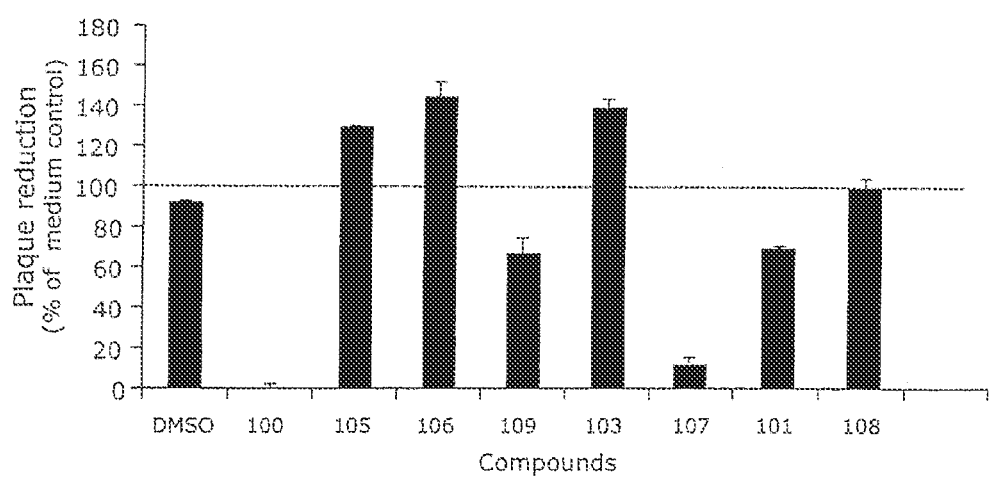

Preliminary analysis of analogs of compound 100 and some of its analogs (see Table 1; compounds 103, 107, 105, 106, 109, 101, and 108) demonstrated that these analogs retain 50-80% activity as compared to compound 100 on LCMV induced IL-8 production (FIGS. 10A, 10B) and LCMV replication (FIG. 10C). These results suggested that the effect of compound 100 on LCMV replication and on NF-κB activity is structure-related.

Example 7B

Compound 100 Inhibits LCMV Replication

Figure 15:
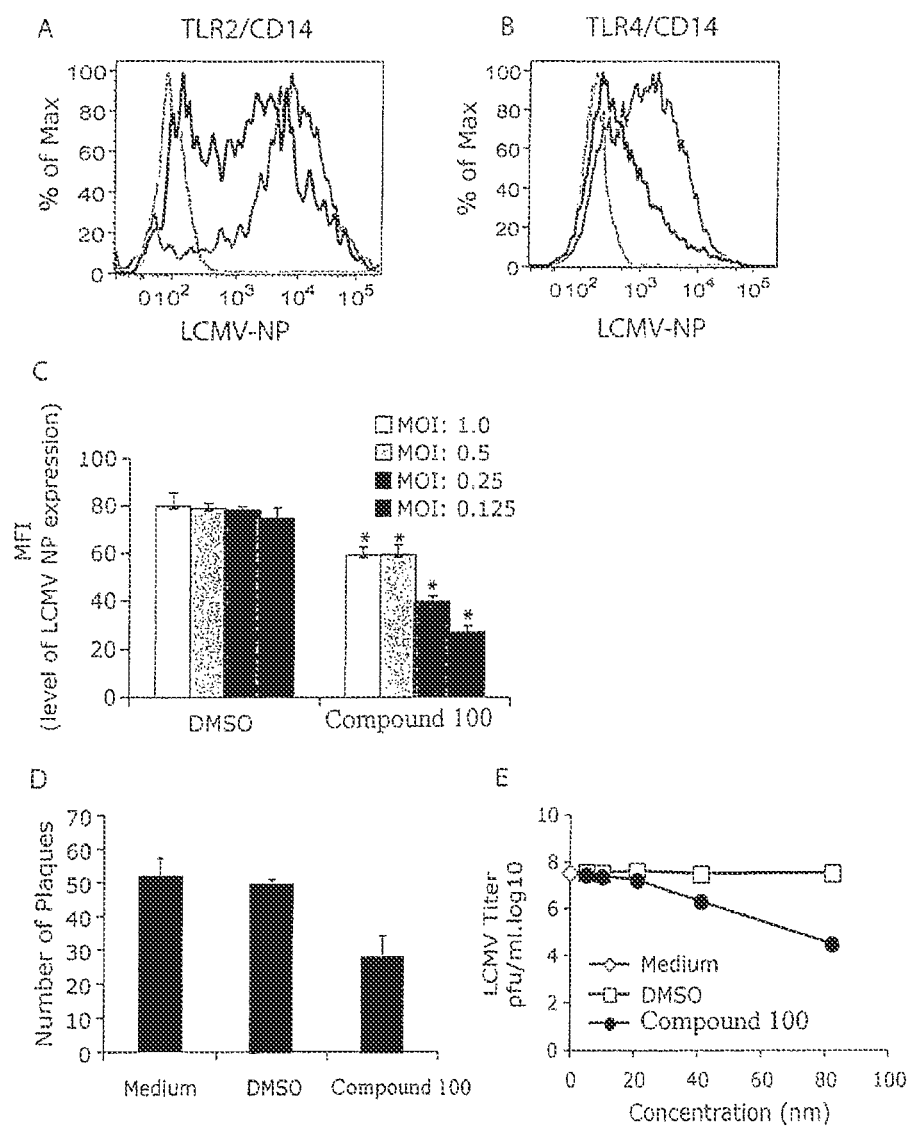
FIG. 15 depicts blockage of LCMV replication by compound 100.

Our previously studies have demonstrated that LCMV replication is critical for a cytokine response but LCMV replication is independent of TLR2 (Zhou et al., 2005). To determine whether compound 100 may also affect LCMV replication, the effect of compound 100 on LCMV replication was evaluated using anti-LCMV NP antibody staining and flow cytometry to monitor the infection. To further define the effect of compound 100 on LCMV replication, Vero cells were utilized, because Vero cells are sensitive to LCMV infection and are commonly used to titrate LCMV. Vero cells were treated with compound 100 (3.3 μM) or DMSO alone, followed by challenge with different amounts of LCMV. LCMV replication was determined by flow cytometry staining of LCMV-NP expression. (FIG. 15A-B). HEK293 cells stably expressing either TLR2/CD14 (SZ10 cells) (A) or TLR4/CD14 (FIG. 15B) were plated in 24-well plate and treated with compound 100 (black lines) or DMSO (grey lines) followed by challenge with LCMV as described in Example 4A. 20 h post-infection, the expression of LCMV NP was determined by flow cytometry staining with VL4 antibody. Grey and tinted area, isotype control. Results are representative of two to three separate experiments. (FIG. 15C) Vero cells were plated in 24-well plates. The next day, cells were treated with compound 100 (3.3 μM) or equal amount of DMSO for 60 min followed by challenge with LCMV at different MOI. After incubation for 1 h, free virus was removed and replaced with fresh medium. Cells were incubated for additional 16-18 h. The expression of LCMV-NP was determined by flow cytometry staining with VL4 antibody and results were shown as the mean fluorescence intensity (MFI) (FIG. 15C). In addition, the replication of LCMV was also determined using the classical plaque assay in Vero cells as described in Example 11 or in Zhou, *Antiviral Research*, 87:295-306 (2010), which is incorporated herein by reference in its entirety, and results were shown as number of plaques (FIG. 15D).

To extend the investigation into the anti-LCMV activity of compound 100, we carried out another experiment in BHK-21 cells. BHK-21 cells are extremely sensitive to LCMV-Arm replication and have been commonly used to propagate LCMV-Arm. The effect of compound 100 on viral replication in BHK-21 cells was determined by plaque assay as described above. BHK-21 cells in 24-well plates were treated with compound 100 or control DMSO as described in Zhou, *Antiviral Research*, 87:295-306 (2010) (FIG. 15E). The virus yield in the supernatants of BHK-21 cells was determined using an immunological focus assay. * $p<0.05$.

Compound 100 dramatically inhibited expression of LCMV-NP (FIG. 15A) and this effect was independent on the expression of TLR2, because compound 100 could also inhibit LCMV replication in HEK cells that did not express TLR2 (FIG. 15B). DMSO had no effect on LCMV replication (FIG. 15A-B). Compound 100 also significantly inhibited LCMV replication in Vero cells evaluated by either flow cytometry staining (expression of LCMV NP) (FIG. 15C) or classic plaque assay (FIG. 15D). Our results further demonstrated that compound 100 inhibited LCMV replication in BHK-21 cells in a dose-dependent manner (FIG. 15E).

Example 8

Compound 100 Inhibits LCMV Induced IL-8 Production in Primary Human Monocytes

Figure 7:
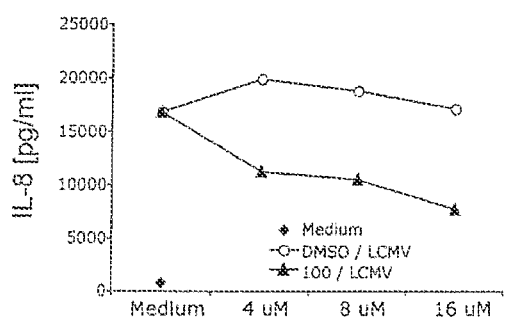
FIG. 7 depicts levels of IL-8 in culture supernatants of human monocytes as measured by ELISA after treatment with compound 100 or DMSO carrier, followed by challenge with LCMV-Arm or human TNF-α.
Figure 7:
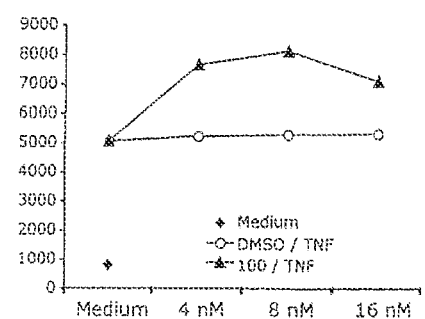

Human monocytes, circulating in the blood stream and sensing the presence of invading microbials, play an important role in both the innate and adaptive immune responses. Human monocytes express a variety of TLRs, including high levels of TLR2. Experiments were performed to determine whether compound 100 could modulate LCMV induced cytokine response in primary human monocytes. In order to compare the effect of compound that we observed in HEK cells (predominantly produce IL-8), the production of IL-8 was measured in primary human monocytes, though they also make other cytokines and chemokines Human peripheral blood mononuclear cells (PBMC) were prepared from buffy coats by lymphocytes separation medium gradient centrifugation. Monocytes were isolated by depletion of non-monocytes (negative selection) using the monocyte isolation kit II (Miltenyi Biotech Inc. Order number: 130-091-153). The purity was about 80% by flow cytometry straining with antibody against CD14. Cells were seeded into 96-well plate (triplicate) at density of $1\times10^4/100$ μl/well in DMEM-10% FCS and treated with compound at various of concentrations. 1 hour post-compound treatment, cells were challenged with medium (negative control), LCMV-Arm, or human TNF-α. After incubation overnight, culture supernatants were collected and the levels of IL-8 were determined by ELISA (OPTEIA ELISA kit, BD Biosciences), following the manufacturer's recommendation. Compound 100 treatment resulted in a significant ($p<0.01$ by two-tailed Student's t test) reduction of LCMV induced IL-8 production compared to DMSO control (FIGS. 7A-7B), and this effect was dose-dependent. These results suggested that compound 100 is functional in primary human monocytes in blocking LCMV induced inflammatory response.

Example 8A

Figure 16:
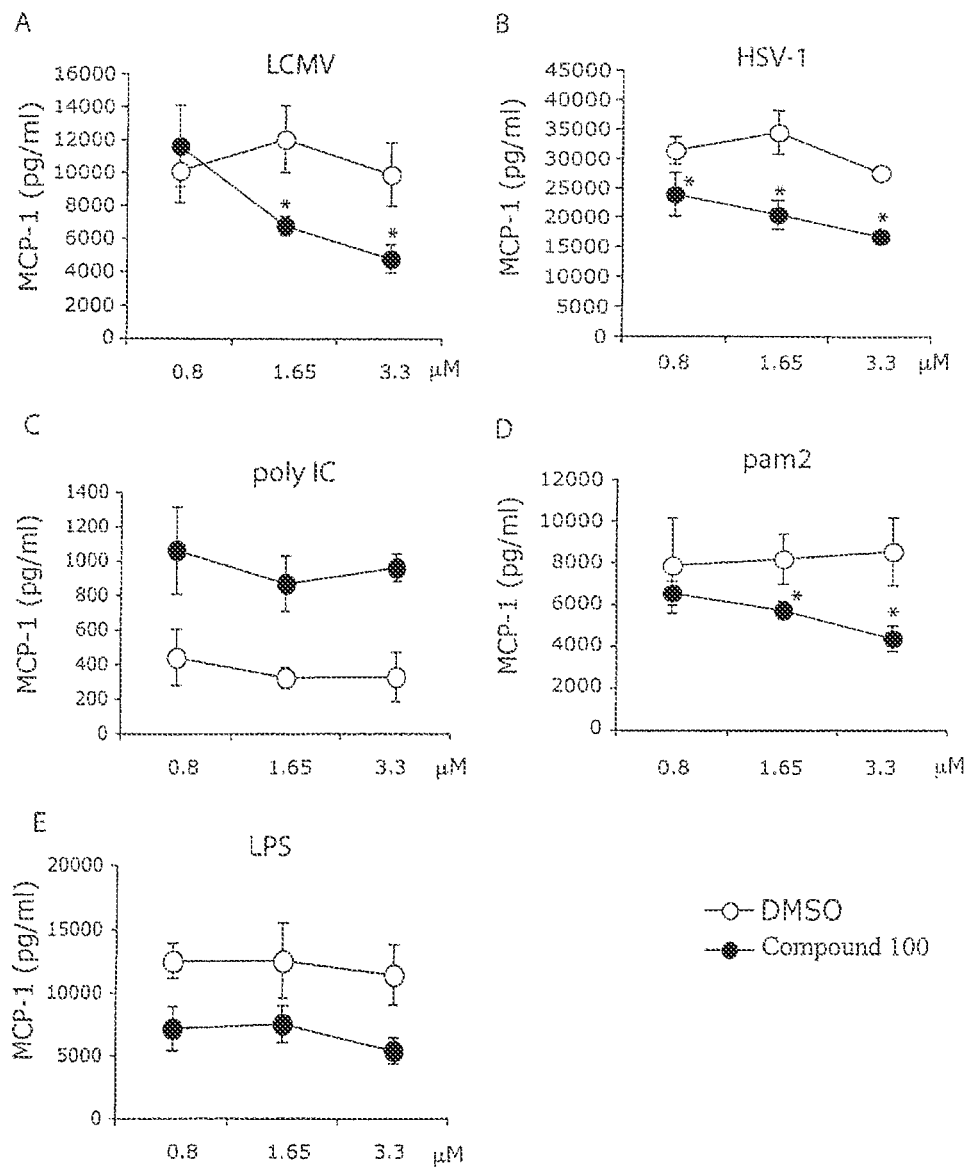
FIG. 16 depicts inhibition of both LCMV and HSV-1-induced MCP-1 production in mouse primary macrophages by compound 100.

Compound 100 Inhibits Both LCMV and HSV Induced Cytokine Responses in Primary Mouse Macrophages Methods: Thioglycollate-elicited peritoneal exudate cells in 96-well plates were treated with compound 100 or DMSO for 60 min followed by challenge with LCMV (FIG. 16A), HSV-1 7134R isolate (WT HSV-1) (FIG. 16B), poly IC (FIG. 16C), pam2 (FIG. 16D), or LPS (FIG. 16E). Cells were incubated for additional 16-18 hr. Levels of MCP-1 in the culture supernatants were measured by ELISA. A representative of three separate experiments. * $p<0.05$.

Figure 17:
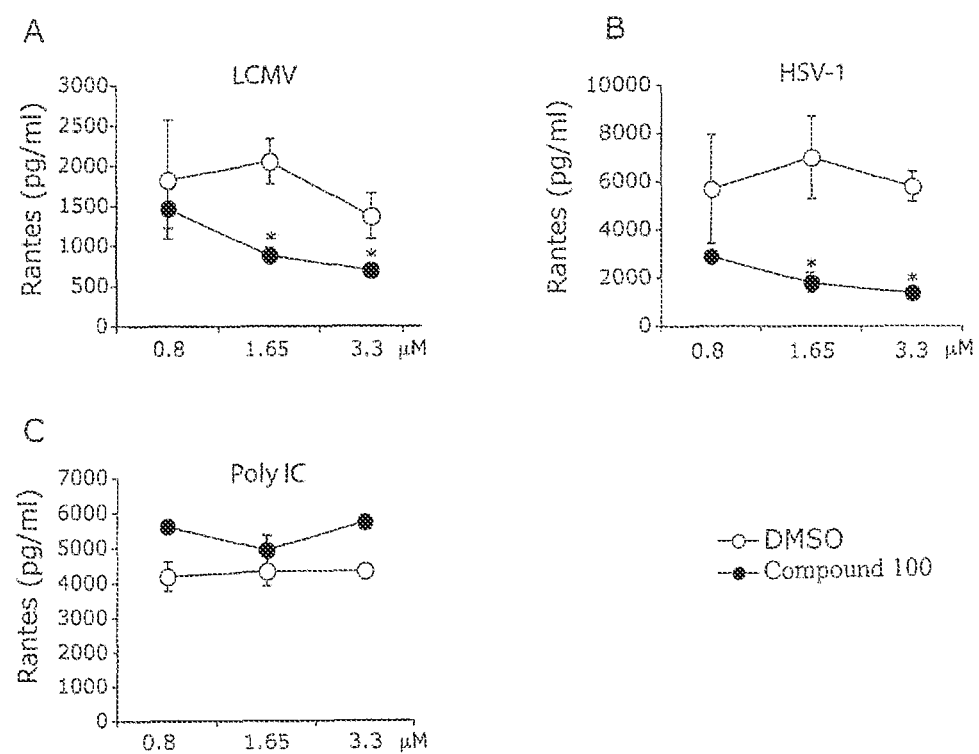
FIG. 17 depicts inhibition of both LCMV and HSV-1-induced RANTES production in mouse primary macrophages by compound 100.

Thioglycollate-elicited peritoneal exudate cells in 96-well plates were treated with compound 100 or DMSO for 60 min followed by challenge with LCMV (FIG. 17A), HSV-1 7134R isolate (WT HSV-1) (FIG. 17B), or poly IC (FIG. 17C). Cells were incubated for additional 16-18 hr. Levels of RANTES in the culture supernatants were measured by ELISA. A representative of three separate experiments. * $p<0.05$.

Results: Macrophages are important inflammatory cells in the host response to virus. To evaluate the effect of compound 100 in modulating cytokine responses in mouse primary macrophages, thioglycollate-elicited peritoneal exudate cells (PECs) isolated from mice and were treated with various doses of compound 100 or DMSO control followed by infection with LCMV. Treatment with compound 100 significantly inhibited LCMV induced production of both MCP-1 (FIG. 7A) and RANTES (FIG. 8A) from mouse macrophages.

Herpes simplex virus 1 (HSV-1) causes a wide array of human diseases from the common herpes labialis or "cold sores" to the more severe, sometimes, lethal herpes encephalitis. It has been previously demonstrated that TLR2 is important in the host response to HSV-1 infection (Kurt-Jones et al., *Proc Natl Acad Sci USA* 101(5), 1315-20 (2004)). To determine whether compound 100 could modulate HSV-1 induced cytokine/chemokine responses in mouse primary macrophages, PECs were treated with compound 100 or DMSO followed by challenge with HSV-1 isolate, 7134R (WT). Interestingly, compound 100 efficiently blocked both HSV-1 induced MCP-1 (FIG. 16B) and RANTES (FIG. 17B) production in mouse macrophages.

Next, we evaluated whether compound 100 could also affect the cytokine responses elucidated by other TLR ligands. Both the TLR2 ligand Pam2CSK4, a synthetic diacylated lipopeptide commonly found in Gram-positive bacteria, and the TLR4 ligand LPS, a cell wall component of Gram-negative bacteria, are able to efficiently induce MCP-1 production (FIG. 16E) in macrophages but induced little RANTES under our experimental conditions. Interestingly, treatment with compound 100 inhibited both Pam2CSK4 and LPS induced MCP-1 production (FIG. 16D-E). In contrast, treatment with compound 100 did not affect poly IC, a synthetic dsRNA and a TLR3 ligand, induced production of either MCP-1 or RANTES (FIG. 16C, 17C).

Example 8B

Compound 100 Inhibits Both LCMV and HSV-1 Induced IL-8 Production in Primary Human Monocytes Methods: Purified primary human monocytes were plated in 96-well plates and treated with compound 100 or DMSO.

Figure 18:
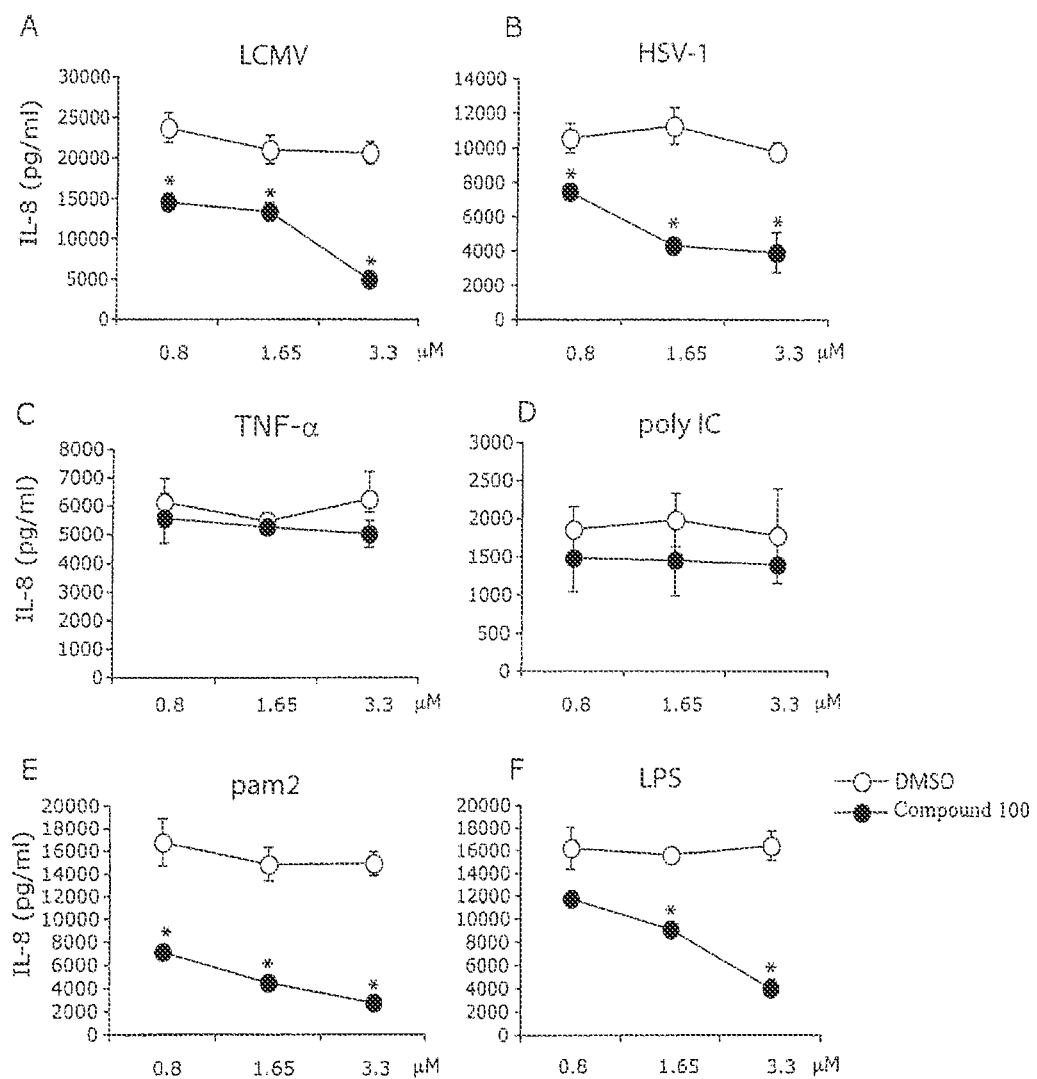
FIG. 18 depicts inhibition of LCMV induced IL-8 production in primary human monocytes by compound 100.

60 min post-compound treatment, cells were challenged with LCMV (FIG. 18A), HSV-1 7134R isolate (WT HSV-1) (FIG. 18B), or the following stimuli: recombinant human TNF-α (FIG. 18C), poly IC (FIG. 18D), pam2 (FIG. 18E), or LPS (FIG. 18F). Cells were incubated for additional 16-18 hr. Levels of IL-8 in the culture supernatants were measured by ELISA. A representative of three individual experiments. * p<0.05.

Results: Human monocytes, circulating in the blood stream and sensing the presence of invading microbials, are important immune cells in both innate and adaptive immune responses. Human monocytes express a variety of TLRs, including high levels of TLR2 (Hornung et al., Nat Med 11(3), 263-70 (2005)). Treatment with compound 100 resulted in a significant reduction of LCMV induced IL-8 production from monocytes compared to DMSO control (FIG. 18A), and this effect was dose-dependent. A similar effect of compound 100 was observed on monocyte production of IL-8 in response to HSV-1 (FIG. 18B), Pam2CSK4 (FIG. 18E), and LPS (FIG. 18F). Interestingly, treatment with compound 100 did not affect either recombinant human TNF-α or poly IC induced production of IL-8 (FIG. 18C-D), demonstrating that the impact of compound 100 on LCMV and HSV-1 induced monocyte IL-8 production is not due to the toxicity of compound.

Example 9

Compound 100 Blocks HSV-induced NF-κB Activation

Figure 11:
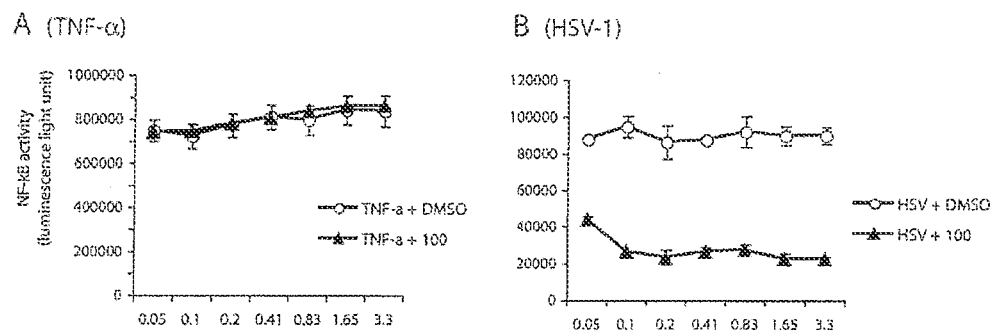
FIG. 11 depicts NF-κB activity (luciferase assay) after treatment with compound 100 or DMSO, following challenge with HSV (FIG. 11B) or control stimulant TNF-α (FIG. 11A).

SZ10 cells were plated and treated with compound 100 or DMSO as described in connection with example 11. Cells were challenged with either HSV (FIG. 11B) or control stimulant TNF-α (FIG. 11A). Cells were incubated for additional 16 hr at 37°, 5% $CO_2$. Cell lysates were used to determine NF-κB activity (luciferase assay). Data are means and standard errors of triplicate wells. Results are representative of three separate experiments.

Example 10

Determination of the Impact of Compound on TLR2 Expression

Figure 8:
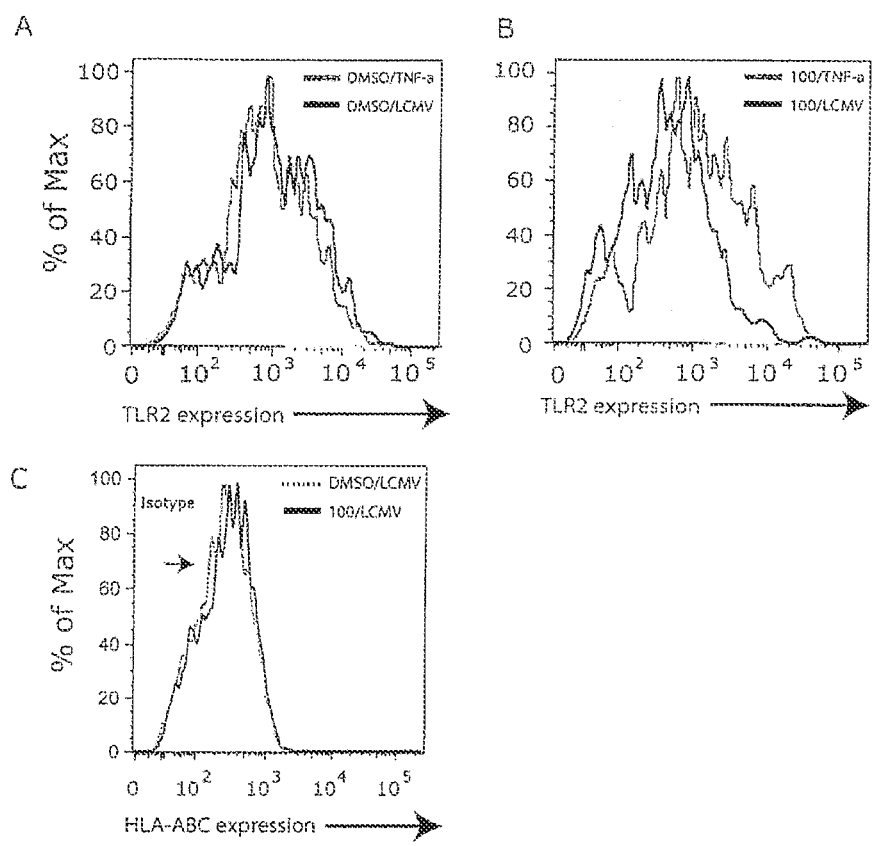
FIG. 8 depicts flow cytometry staining of TNF-α and LCMV induced up-expression of TLR2 after treatment with DMSO (FIG. 8A) and compound 100 (FIG. 8B and showing LCMV-induced TLR2 expression (FIG. 8B) after treatment with DMSO or compound 100 (FIG. 8C).

SZ10 cells were plated into 24-well plate at $1 \times 10^5$/well and incubated overnight at 37° C. in 5% $CO_2$ humidified incubator. Cells were treated with compound or DMSO (compound carrier control). After incubation for 1 hour at 37° C. in 5% $CO_2$ humidified incubator, cells were then challenged with either LCMV-Arm or control TNF-α and were incubated additional 16-18 hours. The expression of TLR2 was determined using flow cytometry staining with anti-human TLR2 (11G7 clone) (FIG. 8). Samples were acquired on a BD-LSR-II flow cytometer (Becton Dickinson). Data were analyzed with FLOWJO software (Tree Star Inc.).

Example 11

Determination of the Effect of Compound on LCMV Replication

Two quantitative methods were utilized to determine the effect of compound on LCMV replication. For the 24-well plate format, Vero cells were seeded at density of $1.5 \times 10^5$/well and incubated overnight until the cells were confluent. The cells were treated with compound or DMSO following the same protocol described in example 9. After being treated with a compound, the cells were challenged with LCMV-Arm. After adsorption for 1 hour at 37° C. in 5% $CO_2$ humidified incubator, virus was removed and replaced with fresh medium. Cells were incubated for 24 h. Virus replication was determined by flow cytometry stain using antibody against LCMV-NP (FIG. 9B). Samples were acquired on a BD-LSR-II flow cytometer (Becton Dickinson). Data were analyzed with Flowjo software (Tree Star Inc.). For 6-well plate format, Vero cells were seeded at density of $5 \times 10^5$/well and incubated overnight until cells were 100% confluent. Cells were similarly treated with compound or DMSO. After treatment, cells were challenged with LCMV-Arm at 50 pfu/well. After adsorption for 1 hour at 37° C. in 5% $CO_2$ humidified incubator, virus was removed and replaced with a mixture of complete 2×M199/10% FCS and 1% agarose. 3-4 days after incubation, the secondary overlay mixture of 2×M199/10% FCS and 1% agarose containing neutral red was added. After incubation for an additional 4-6 hours or overnight at 37° C. in a 5% $CO_2$ humidified incubator, plaques were counted using a lightbox. Results were shown as % plaque reduction (FIG. 9C). The plaque reduction was calculated as follows. Per cent plaque reduction=number of plaques in compound treated cells number of plaques in DMSO treated cells/number of plaques in DMSO treated cells×100%.

Example 12

Animal Studies in Mice Show Inhibition of Cytokine Induction in Vivo

Figure 12:
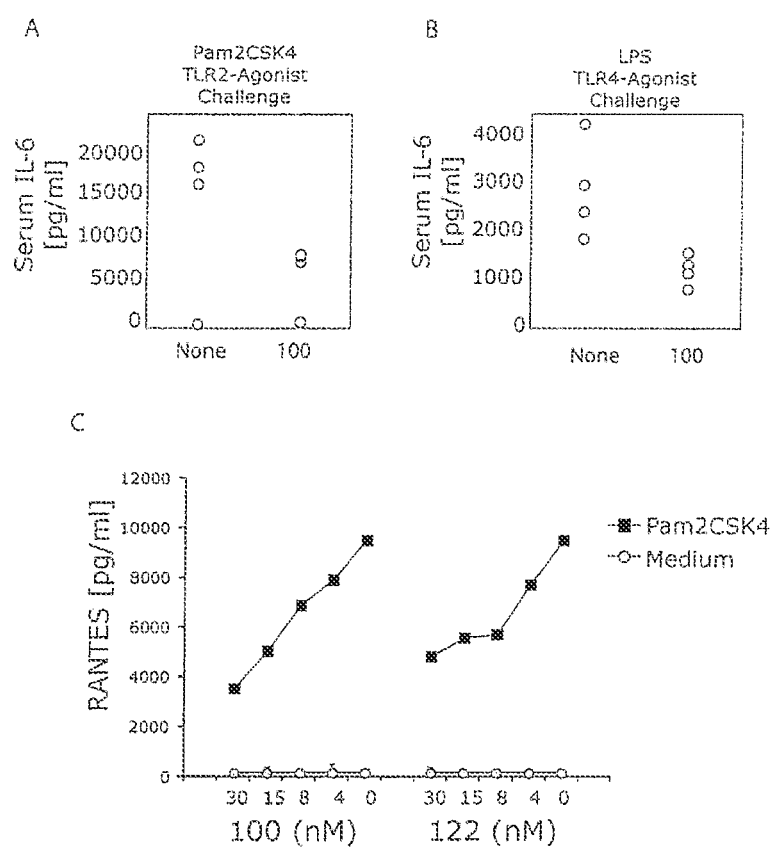
FIG. 12 depicts serum IL-6 in mice challenged with Pam$_2$CSK$_4$ or LPS and treated with compound 100 or carrier (FIG. 12A, 12B) and RANTES production by macrophages from mice challenged with Pam$_2$CSK$_4$ and treated with compound 100 (FIG. 12C).

Preliminary animal studies performed on mice indicate that there was no apparent toxic effect when mice were injected intravenously at 16.67 mg/kg (200 µg/mouse) with compound 100. Compound 100 inhibits LPS and $Pam_2CSK_4$ induced cytokine (Interleukin-6 and IL-6) induction in vivo (FIG. 12A, B). In addition, compounds 100 and 122 can also inhibit $Pam_2CSK_4$ induced RANTES in vitro in macrophages (FIG. 12C).

Example 13

Compound 100 Inhibits LCMV-induced Inflammation in a Mouse Model

Figure 13:
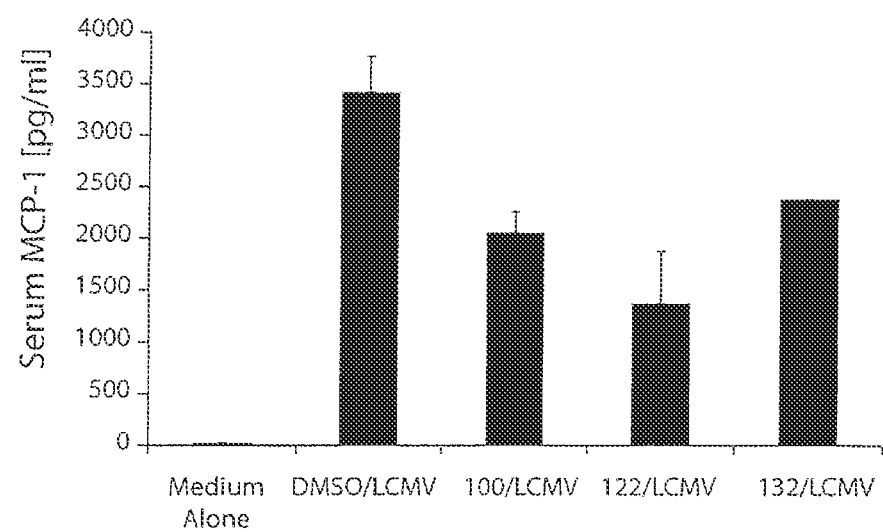
FIG. 13 depicts serum MCP-1 in mice infected with LCMV and treated with compound 100, 122, 132 or carrier.

Briefly, compound was administered to mice through tail vein (i.v.) at 16.67 mg/kg (200 µg/mouse). 10 min after pretreatment with compound 100, 122 or 132, the mice were challenged with LCMV-Arm via intraperitoneal injection (i.p.). Serum samples were collected at 20 h and 48 h post-infection. Serum levels of MCP-1 were determined by ELISA. (FIG. 13).

Example 13A

Compound 100 Blocks LCMV and Other TLR Ligands Induced Inflammation In Vivo

Figure 19:
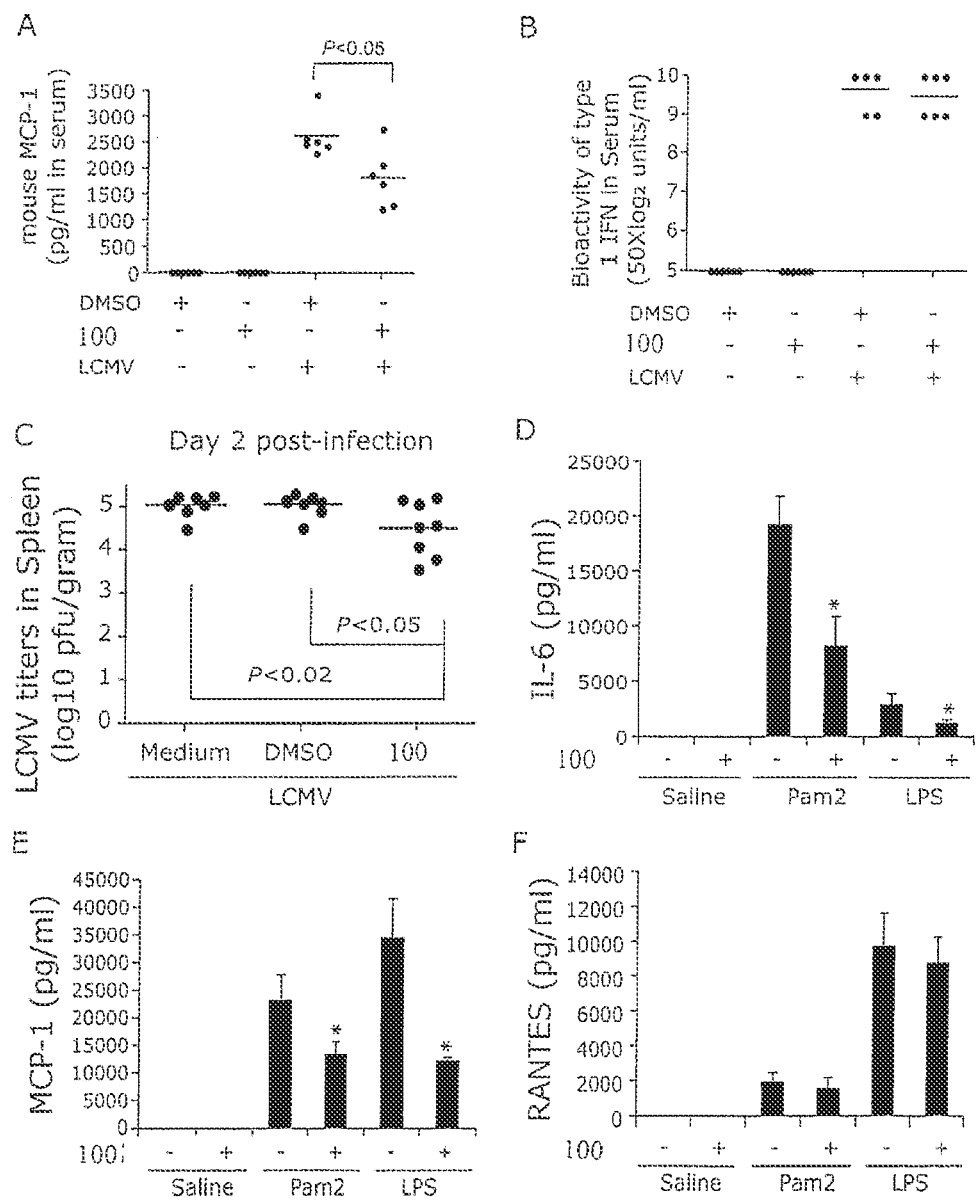
FIG. 19 depicts inhibition of both LCMV and other TLR ligands induced cytokine production and viral replication in vivo by compound 100.

Methods: C57BL/6 mice were injected i.p. with compound 100 at 400 µg/mouse or DMSO. Within 20 min post-treatment, mice were challenged with LCMV-Arm ($2 \times 10^5$ pfu). 18 h post-infection, levels of MCP-1 in serum were determined by ELISA (FIG. 19A) and the bioactivity of type I IFN was measured by type I IFN bioassay (FIG. 19B). To determine if compound 100 inhibits LCMV replication in vivo, groups of 8 C57BL/6 mice were treated as described in the Materials and Methods. Mice were sacrificed 48 h post-infection and spleens were collected. Virus titers in spleens were determined using an immunofocus assay with antibody against LCMV NP (VL4). Spleen viral titers in individual mice were shown (n=8) (FIG. 19C). C57BL/6 mice were intravenously injected with compound 100 at 400 μg/mouse or DMSO. Within 10 min post-treatment, mice were challenged with either pam2CSK (0.8 mg/kg) or LPS (0.8 mg/kg). Six hrs post-infection, levels of IL-6 (FIG. 19D), MCP-1 (FIG. 19E), or RANTES (FIG. 19F) in serum were determined by ELISA. * p<0.05.

Results: To evaluate the effect of compound 100 on inhibition of LCMV induced inflammation in vivo, C57BL/6J mice were pre-treated with DMSO or compound 100 once via intravenous route at 400 μg/mouse (16 mg/kg) followed by challenge with LCMV-Arm via intraperitoneal administration. Treatment with a single dose of compound 100 resulted in a significant decrease in LCMV induced MCP-1 production as compared with levels in DMSO treated compound 100 mice (FIG. 19A). In contrast, compound 100 treatment did not affect LCMV induced type I IFN production (FIG. 19B). Compound 100-treated mice had significantly lower levels of virus (p<0.05) in the representative organ, the spleen, compared to DMSO-treated or untreated mice (FIG. 19C). Interestingly, compound 100 treatment also significantly blocked both TLR2 ligand Pam2CSK4 and TLR4 ligand LPS induced IL-6 and MCP-1 production (FIG. 19D-E). In contrast, compound 100 did not affect either Pam2CSK4 or LPS-induced RANTES production (FIG. 19F).

Example 14

Compound 100 Inhibits HSV-1

Figure 20:
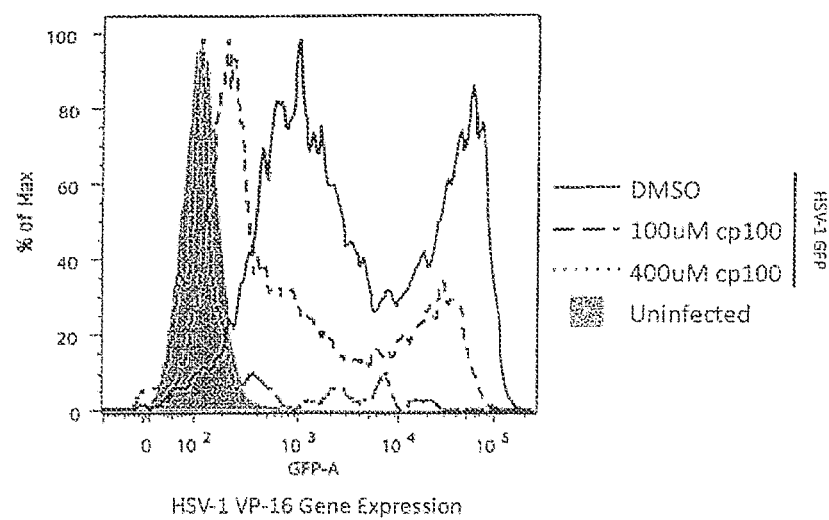
FIG. 20 depicts GFP fluorescence intensity for Vero cells inoculated with HSV with data shown as a histogram, depicting the percentage of maximum cell count as a function of GFP-A fluorescence.

HSV-1 is a DNA virus. Compound 100 inhibits HSV-1 replication in a dose-dependent manner. Vero cells were inoculated with HSV (VP16-GFP strain, multiplicity of infection=2) in serum-free DMEM media for 1 hour at 37 C. Cells were then washed with 1×PBS, and incubated in complete media supplemented with 10% fetal calf serum and compound 100 at the specified concentration for 24 hours. Cell were then washed with 1×PBS, suspended with trypsin, and fixed for 30 minutes with 4% formalin. Cells were immediately analyzed for GFP fluorescence intensity using a BD LSRII flow cytometer. Viable cells were isolated based on SSC-A and FSC-A. Data is shown as a histogram, depicting the percentage of maximum cell count as a function of GFP-A fluorescence (FIG. 20).

Figure 21:
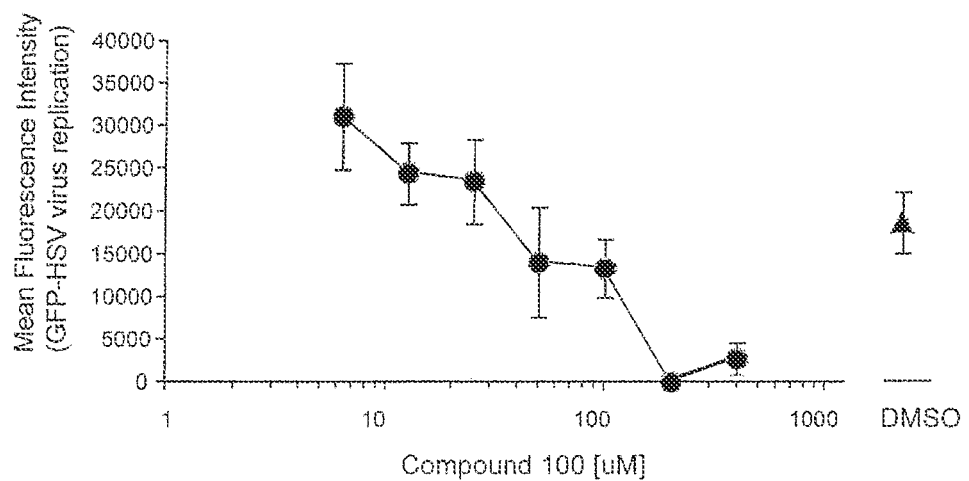
FIG. 21 depicts GFP fluorescence intensity for Vero cells were inoculated with HSV with data shown as corrected for background fluorescence of uninfected cells.

Vero cells were inoculated with HSV (VP16-GFP strain, multiplicity of infection=1) in serum-free DMEM media for 1 hour at 37 C. Cells were then washed with 1×PBS, and incubated in complete media supplemented with 10% fetal calf serum and compound 100 at the specified concentration for 24 hours. Cell were then washed with 1×PBS, and fixed for 30 mins with 4% formalin. Mean GFP fluorescence intensity of each well was measured using a Perkin Elmer EnVision multilabel plate reader. Data shown was corrected for background fluorescence of uninfected cells. Error bars represent SD around the mean, n=3 (FIG. 21).

Example 15

Compound 100 Inhibits Tacaribe Virus and Rift Valley Fever Virus

Compound 100 inhibits Tacaribe virus and Rift Valley Fever Virus (RVFV), two RNA Arenaviruses. The antiviral activity of compound 100 was evaluated against two human viruses: Tacaribe virus (a member of human new Arenaviruses. Scientific name, Tacaribe virus. Common name, TCRV) and Rift Valley Fever Virus (RVFV), in the laboratory at Institute for Antiviral Research, Department of Animal, Dairy, and Veterinary Sciences, Utah State University.

Using an approach designated as "Virus Yield Reduction (VYR)", the effect of compound 100 on reduction of virus yield was evaluated by assaying frozen and thawed eluates from each cup for virus titer by serial dilution onto monolayers of susceptible cells (Vero cells for TCRV and Vero 76 cells for RVFV). A known active drug (Ribavirin) was run in parallel as a positive control. The 90% effective concentration (EC90), which is that test drug concentration that inhibits virus yield by 1 log 10, is determined from these data. A 50% cell inhibitory (cytotoxic) concentration (CC50) is determined by regression analysis of these data. Each test compound's antiviral activity is expressed as a Selectivity Index (SI), which is the EC90 divided by the CC50 (SI=CC50÷EC90). Generally, an SI of 10 or greater is indicative of positive antiviral activity, although other factors, such as a low SI for the positive control, are also taken into consideration.

The following results demonstrated that compound 100 can inhibit the replication and production of TCRV, a member of human new Arenaviruses. In contrast, this compound has no role against another human virus, RVFV.

TCRV (Vero)—3-day Virus Yield Reduction (VYR) Assay
Expt 1—EC90=1.3, CC50=8.6, SI=6.6
Expt 2—EC90=3.7, CC50=15, SI=4.1
RVFV (Vero 76)—3-day Virus Yield Reduction (VYR) Assay
Expt 1—EC90=>8.9, CC50=8.9, SI=0
Expt 2—EC90=>18, CC50=18, SI=0
Thus, Examples 14 and 15 demonstrate that compound 100 is active as an antiviral to both major classes of viruses, DNA viruses and RNA viruses.

TABLE 1

| Compound # | Structure | % Inhibition * | Optimal Dose | 50% Inhibitory Dose |
|---|---|---|---|---|
| 100 | 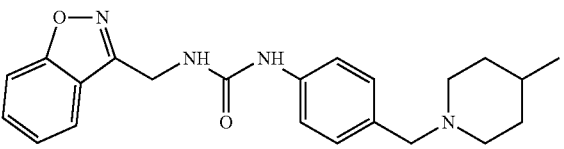 [SMILES: CC1CCN(Cc2ccc(NC(=O)NCc3noc4ccccc34)cc2)CC1] | 80 | 3.3 | 1.0 |

TABLE 1-continued

| Compound # | Structure | % Inhibition * | Optimal Dose | 50% Inhibitory Dose |
|---|---|---|---|---|
| 101 | 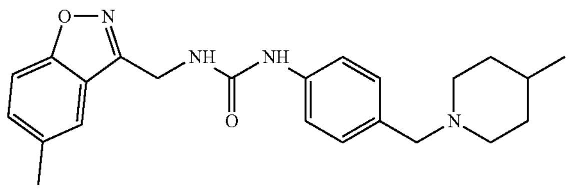 [SMILES: Cc1ccc2onc(CNC(=O)Nc3ccc(CN4CCC(C)CC4)cc3)c2c1] | 60 | 3.3 | 1.6 |
| 102 | 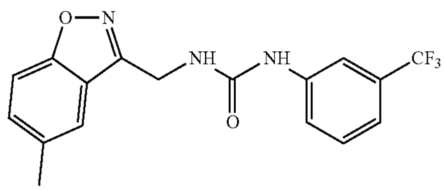 [SMILES: Cc1ccc2onc(CNC(=O)Nc3cccc(C(F)(F)F)c3)c2c1] | 27 | 3.3 | >6.6 |
| 103 | 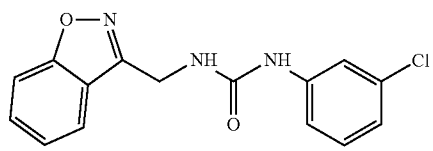 [SMILES: O=C(NCc1noc2ccccc12)Nc1cccc(Cl)c1] | 26 | 3.3 | >6.6 |
| 105 | 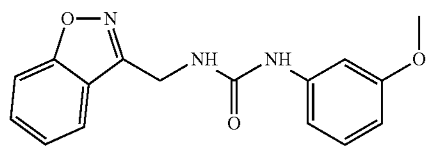 [SMILES: COc1cccc(NC(=O)NCc2noc3ccccc23)c1] | 20 | 3.3 | >6.6 |
| 106 | 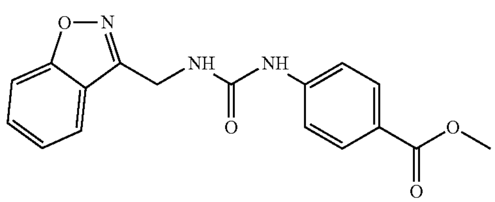 [SMILES: COC(=O)c1ccc(NC(=O)NCc2noc3ccccc23)cc1] | 75 | 3.3 | 1.6 |
| 107 | 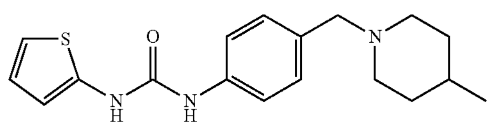 [SMILES: CC1CCN(Cc2ccc(NC(=O)Nc3cccs3)cc2)CC1] | 47 | 3.3 | 3.0 |
| 108 | 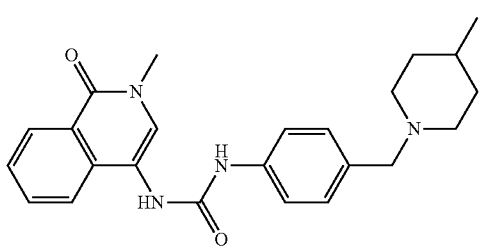 [SMILES: CC1CCN(Cc2ccc(NC(=O)Nc3cn(C)c(=O)c4ccccc34)cc2)CC1] | 39 | 3.3 | >6.6 |
| 109 | 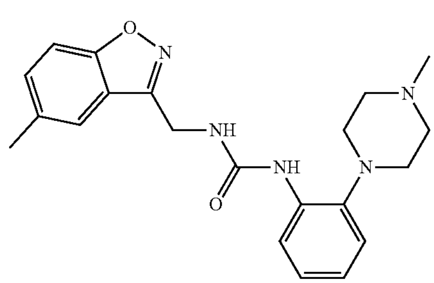 | 39 | 3.3 | >6.6 |

TABLE 1-continued

| Compound # | Structure | % Inhibition* | Optimal Dose | 50% Inhibitory Dose |
|---|---|---|---|---|
| 110 | 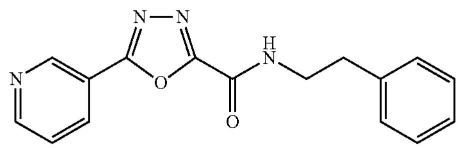 [SMILES: O=C(NCCc1ccccc1)c1nnc(-c2cccnc2)o1] | 40 | 3.3 | >6.6 |
| 112 | 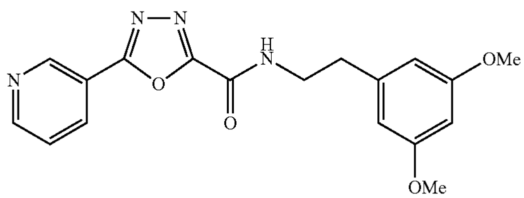 [SMILES: COc1cc(CCNC(=O)c2nnc(-c3cccnc3)o2)cc(OC)c1] | 65 | 1.6 | 0.4 |
| 113 | 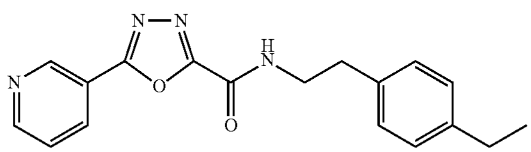 [SMILES: CCc1ccc(CCNC(=O)c2nnc(-c3cccnc3)o2)cc1] | 30 | 1.6 | >6.6 |
| 114 | 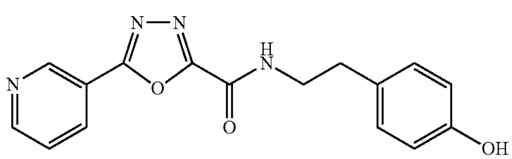 [SMILES: O=C(NCCc1ccc(O)cc1)c1nnc(-c2cccnc2)o1] | 31 | 0.8 | >6.6 |
| 115 | 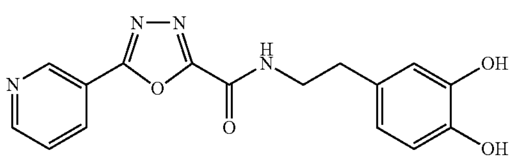 [SMILES: O=C(NCCc1ccc(O)c(O)c1)c1nnc(-c2cccnc2)o1] | 40 | 1.6 | >6.6 |
| 116 | 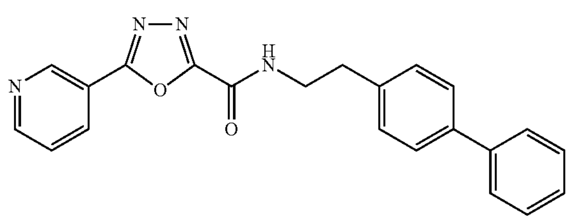 [SMILES: O=C(NCCc1ccc(-c2ccccc2)cc1)c1nnc(-c2cccnc2)o1] | 50 | 0.8 | 0.8 |
| 117 | 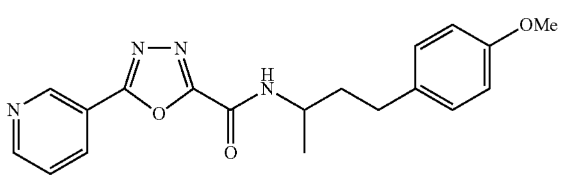 [SMILES: COc1ccc(CCC(C)NC(=O)c2nnc(-c3cccnc3)o2)cc1] | 27 | 0.8 | >6.6 |
| 118 | 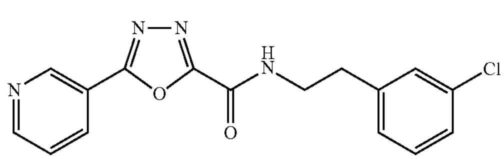 [SMILES: O=C(NCCc1cccc(Cl)c1)c1nnc(-c2cccnc2)o1] | 50 | 3.3 | 3.3 |
| 119 | 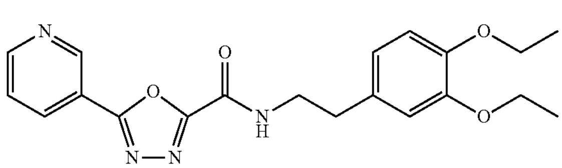 [SMILES: CCOc1ccc(CCNC(=O)c2nnc(-c3cccnc3)o2)cc1OCC] | 70 | 3.3 | 0.8 |

TABLE 1-continued

| Compound # | Structure | % Inhibition * | Optimal Dose | 50% Inhibitory Dose |
|---|---|---|---|---|
| 120 | 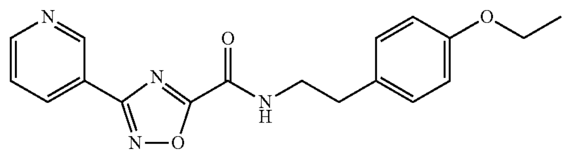 [SMILES: CCOc1ccc(CCNC(=O)c2nc(-c3cccnc3)no2)cc1] | 75 | 3.3 | 0.8 |
| 121 | 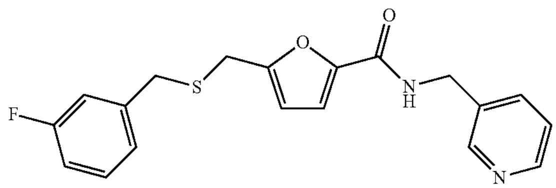 [SMILES: O=C(NCc1cccnc1)c1ccc(CSCc2cccc(F)c2)o1] | 60 | 3.3 | 0.8 |
| 122 | 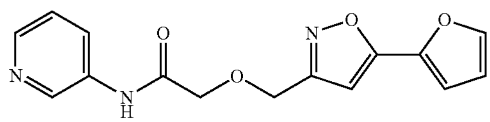 [SMILES: O=C(COCc1cc(-c2ccco2)on1)Nc1cccnc1] | 50 | 3.3 | 3.3 |
| 125 | 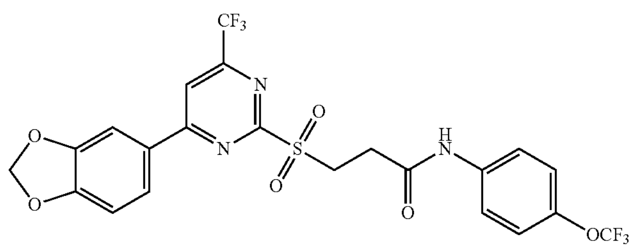 [SMILES: O=C(CCS(=O)(=O)c1nc(-c2ccc3c(c2)OCO3)cc(C(F)(F)F)n1)Nc1ccc(OC(F)(F)F)cc1] | 60 | 3.3 | 0.8 |
| 132 | 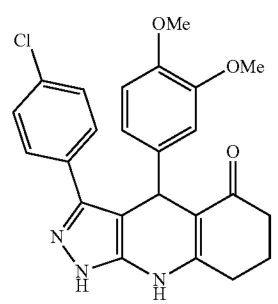 [SMILES: COc1ccc(C2C3=C(CCCC3=O)Nc3[nH]nc(-c4ccc(Cl)cc4)c32)cc1OC] | 75 | 3.3 | 0.8 |
| 133 | 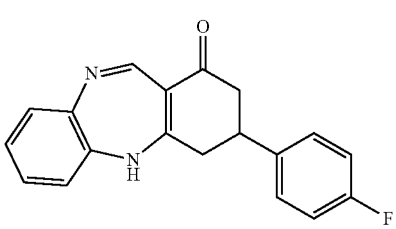 [SMILES: O=C1CC(c2ccc(F)cc2)CC2=C1C=Nc1ccccc1N2] | 60 | 1.6 | 0.8 |

TABLE 1-continued

| Compound # | Structure | % Inhibition* | Optimal Dose | 50% Inhibitory Dose |
|---|---|---|---|---|
| 134 | 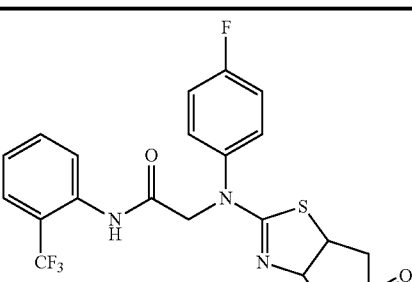 | 50 | 1.6 | 1.6 |
| 135 | 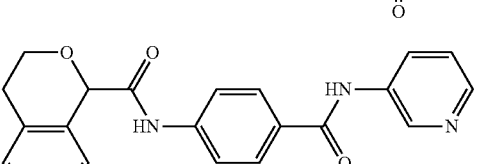 | 60 | 3.3 | 0.8 |

*Determined by the assay in Example 4

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating an inflammatory condition selected from chronic joint disease, chronic active gastritis, chronic mucosal inflammation, and sepsis in an individual in need thereof, comprising administering to said individual a therapeutically effective amount of a compound of Formula I:

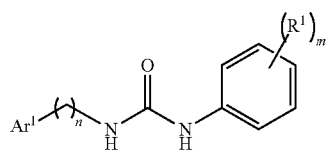

I or a pharmaceutically acceptable salt thereof, wherein:
Ar$^1$ is selected from:

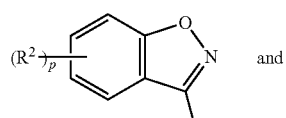

and

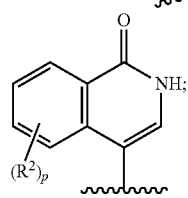

each R$^1$ is independently selected from —OR$^a$, —SR$^b$, —C(O)R$^b$, —C(O)NR$^e$R$^f$, —C(O)OR$^a$, —OC(O)R$^b$, —OC(O)NR$^e$R$^f$, —NR$^e$R$^f$, —NR$^c$C(O)R$^d$, —NR$^c$C(O)OR$^d$, —NR$^c$C(O)NR$^d$, —S(O)R$^b$, —S(O)NR$^e$R$^f$, —S(O)$_2$R$^a$, —NR$^c$S(O)$_2$R$^d$, halogen, cyano, nitro, C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl; wherein said C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl are each optionally substituted by 1, 2, 3, or 4 independently selected R$^{1'}$ groups;

each R$^2$ is independently selected from —OR$^m$, —SR$^n$, —C(O)R$^n$, —C(O)NR$^qR^r$, —C(O)OR$^m$, —OC(O)R$^n$, —OC(O)NR$^qR^r$, —NR$^qR^r$, —NR$^o$C(O)R$^p$, —NR$^o$C(O)OR$^p$, —NR$^o$C(O)NR$^p$, —S(O)R$^n$, —S(O)NR$^qR^p$, —S(O)$_2$R$^m$, —NR$^o$S(O)$_2$R$^p$, halogen, cyano, nitro, C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl; wherein said C$_{1-6}$ alkyl, C$_{2-6}$ alkenyl, C$_{2-6}$ alkynyl, C$_{1-6}$ haloalkyl, C$_{3-10}$ cycloalkyl, C$_{3-10}$ cycloalkyl-C$_{1-3}$ alkyl, C$_{2-9}$ heterocycloalkyl, C$_{2-9}$ heterocycloalkyl-C$_{1-3}$ alkyl, C$_{6-10}$ aryl, C$_{6-10}$ aryl-C$_{1-3}$ alkyl, C$_{1-9}$ heteroaryl, and C$_{1-9}$ heteroaryl-C$_{1-3}$ alkyl are each optionally substituted by 1, 2, 3, or 4 independently selected R$^{2'}$ groups;

each R$^b$ and R$^n$ is independently selected from C$_{1-6}$ alkyl, C$_{2-6}$ alkenyl, C$_{2-6}$ alkynyl, C$_{1-6}$ haloalkyl, C$_{3-7}$ cycloalkyl, C$_{3-7}$ cycloalkyl-C$_{1-3}$ alkyl, C$_{2-6}$ heterocycloalkyl, C$_{2-6}$ heterocycloalkyl-C$_{1-3}$ alkyl, phenyl, phenyl-C$_{1-3}$ alkyl, C$_{1-6}$ heteroaryl, and C$_{1-6}$ heteroaryl-C$_{1-3}$ alkyl; wherein said C$_{1-6}$ alkyl, C$_{2-6}$ alkenyl, C$_{2-6}$ alkynyl, C$_{1-6}$ haloalkyl, C$_{3-7}$ cycloalkyl, C$_{3-7}$ cycloalkyl-C$_{1-3}$ alkyl, C$_{2-6}$ heterocycloalkyl, C$_{2-6}$ heterocycloalkyl-C$_{1-3}$ alkyl, phenyl, phenyl-C$_{1-3}$ alkyl, C$_{1-6}$ heteroaryl, and C₁₋₆ heteroaryl-C₁₋₃ alkyl are each optionally substituted by 1, 2, 3, or 4 independently selected R^g groups;

each R^a, R^c, R^d, R^e, R^f, R^m, R^o, R^p, R^r, and R^q is independently selected from H, C₁₋₆ alkyl, C₂₋₆ alkenyl, C₂₋₆ alkynyl, C₁₋₆ haloalkyl, C₃₋₇ cycloalkyl, C₃₋₇ cycloalkyl-C₁₋₃ alkyl, C₂₋₆ heterocycloalkyl, C₂₋₆ heterocycloalkyl-C₁₋₃ alkyl, phenyl, phenyl-C₁₋₃ alkyl, C₁₋₆ heteroaryl, and C₁₋₆ heteroaryl-C₁₋₃ alkyl; wherein said C₁₋₆ alkyl, C₂₋₆ alkenyl, C₂₋₆ alkynyl, C₁₋₆ haloalkyl, C₃₋₇ cycloalkyl, C₃₋₇ cycloalkyl-C₁₋₃ alkyl, C₂₋₆ heterocycloalkyl, C₂₋₆ heterocycloalkyl-C₁₋₃ alkyl, phenyl, phenyl-C₁₋₃ alkyl, C₁₋₆ heteroaryl, and C₁₋₆ heteroaryl-C₁₋₃ alkyl are each optionally substituted by 1, 2, 3, or 4 independently selected R^g groups;

each R^1', R^2', and R^g is independently selected from halogen, cyano, nitro, hydroxyl, carboxy, C₁₋₄ alkyl, C₁₋₄ haloalkyl, C₁₋₄ alkoxy, C₁₋₄ haloalkoxy, C₂₋₄ alkenyl, C₂₋₄ alkynyl, C₁₋₄ alkylcarbonyl, C₁₋₄ alkoxycarbonyl, amino, C₁₋₄ alkylamino, di-C₁₋₄ alkylamino, and C₁₋₄ alkylsulfonyl;

n is an integer selected from 0, 1, and 2; and m and p are each independently an integer selected from 0, 1, 2, 3, 4, and 5; provided that the proper valencies are not exceeded.

2. The method according to claim 1, wherein each R² is independently selected from halogen, cyano, nitro, hydroxyl, carboxy, C₁₋₄ alkyl, C₁₋₄ haloalkyl, C₁₋₄ alkoxy, C₁₋₄ haloalkoxy, C₂₋₄ alkenyl, C₂₋₄ alkynyl, C₁₋₄ alkylcarbonyl, C₁₋₄ alkoxycarbonyl, amino, C₁₋₄ alkylamino, di-C₁₋₄ alkylamino, and C₁₋₄ alkylsulfonyl.

3. The method according to claim 1, wherein each R² is independently selected from C₁₋₆ alkyl.

4. The method according to claim 1, wherein p is 0 or 1.

5. The method according to claim 1, wherein Ar¹ is selected from:

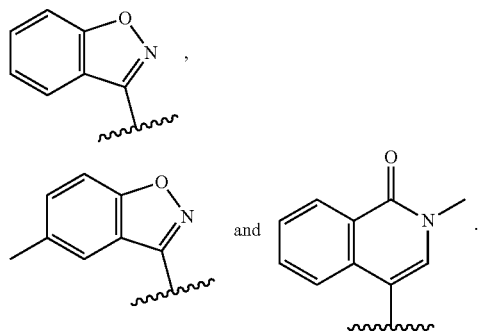

6. The method according to claim 1, wherein each R¹ is independently selected from —OR^a, —C(O)R^b, —C(O)NR^eR^f, —C(O)OR^a, —NR^eR^f, —NR^cC(O)R^d, —S(O)₂R^a, halogen, cyano, nitro, C₁₋₆ alkyl, C₁₋₆ haloalkyl, C₃₋₁₀ cycloalkyl, C₃₋₁₀ cycloalkyl-C₁₋₃ alkyl, C₂₋₉ heterocycloalkyl, and C₂₋₉ heterocycloalkyl-C₁₋₃ alkyl; wherein said C₁₋₆ alkyl, C₁₋₆ haloalkyl, C₃₋₁₀ cycloalkyl, C₃₋₁₀ cycloalkyl-C₁₋₃ alkyl, C₂₋₉ heterocycloalkyl, and C₂₋₉ heterocycloalkyl-C₁₋₃ alkyl are each optionally substituted by 1, 2, 3, or 4 independently selected R^1' groups.

7. The method according to claim 1, wherein each R¹ is independently selected from —OR^a, —C(O)OR^a, halogen, C₁₋₆ haloalkyl, C₂₋₉ heterocycloalkyl, and C₂₋₉ heterocycloalkyl-C₁₋₃ alkyl, wherein said C₂₋₉ heterocycloalkyl, and C₂₋₉ heterocycloalkyl-C₁₋₃ alkyl are each optionally substituted with 1, 2, 3, or 4 independently selected R^1' groups.

8. The method according to claim 1, wherein each R¹ is independently selected from chloro, trifluoromethyl, methoxy, methoxycarbonyl, 4-methylpiperazinyl, and (4-methylpiperidinyl)methyl.

9. The method according to claim 1, wherein each R^1' is independently C₁₋₄ alkyl.

10. The method according to claim 1, wherein m is 0, 1, or 2.

11. The method according to claim 1, wherein n is 0.

12. The method according to claim 1, wherein n is 1.

13. The method according to claim 1, wherein:

Ar¹ is selected from:

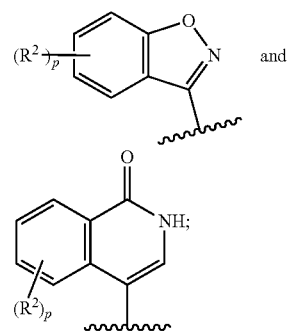

each R² is independently selected from halogen, cyano, nitro, hydroxyl, carboxy, C₁₋₄ alkyl, C₁₋₄ haloalkyl, C₁₋₄ alkoxy, C₁₋₄ haloalkoxy, C₂₋₄ alkenyl, C₂₋₄ alkynyl, C₁₋₄ alkylcarbonyl, C₁₋₄ alkoxycarbonyl, amino, C₁₋₄ alkylamino, di-C₁₋₄ alkylamino, and C₁₋₄ alkylsulfonyl;

each R¹ is independently selected from —OR^a, —C(O)R^b, —C(O)NR^eR^f, —C(O)OR^a, —NR^eR^f, —NR^cC(O)R^d, —S(O)₂R^a, halogen, cyano, nitro, C₁₋₆ alkyl, C₁₋₆ haloalkyl, C₃₋₁₀ cycloalkyl, C₃₋₁₀ cycloalkyl-C₁₋₃ alkyl, C₂₋₉ heterocycloalkyl, and C₂₋₉ heterocycloalkyl-C₁₋₃ alkyl; wherein said C₁₋₆ alkyl, C₁₋₆ haloalkyl, C₃₋₁₀ cycloalkyl, C₃₋₁₀ cycloalkyl-C₁₋₃ alkyl, C₂₋₉ heterocycloalkyl, and C₂₋₉ heterocycloalkyl-C₁₋₃ alkyl are each optionally substituted by 1, 2, 3, or 4 independently selected R^1' groups;

each R^1' is independently C₁₋₄ alkyl;

m is 0, 1, or 2;

n is 0 or 1; and p is 0 or 1.

14. The method according to claim 1, wherein:

Ar¹ is selected from:

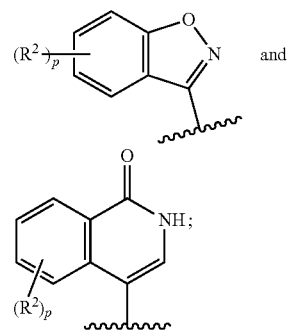

each R² is independently selected from C₁₋₆ alkyl;

each R¹ is independently selected from —OR^a, —C(O)OR^a, halogen, C₁₋₆ haloalkyl, C₂₋₉ heterocycloalkyl, and $C_{2-9}$ heterocycloalkyl-$C_{1-3}$ alkyl, wherein said $C_{2-9}$ heterocycloalkyl, and $C_{2-9}$ heterocycloalkyl-$C_{1-3}$ alkyl are each optionally substituted with 1, 2, 3, or 4 independently selected $R^{1'}$ groups;

each $R^{1'}$ is independently $C_{1-4}$ alkyl;

each $R^a$ is independently selected from H and $C_{1-6}$ alkyl;

m is 0, 1, or 2;

n is 0 or 1; and p is 0 or 1.

15. The method according to claim 1, wherein:

$Ar^1$ is selected from:

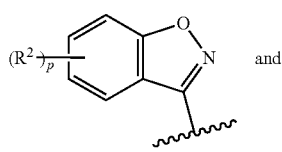 and

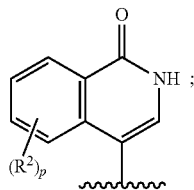

each $R^2$ is independently selected from methyl;

each $R^1$ is independently selected from chloro, trifluoromethyl, methoxy, methoxycarbonyl, 4-methylpiperazinyl, and (4-methylpiperidinyl)methyl;

m is 0, 1, or 2;

n is 0 or 1; and p is 0 or 1.

16. The method according to claim 1, wherein $Ar^1$ is:

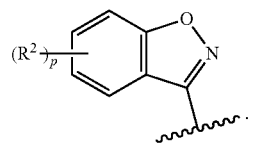

17. The method according to claim 1, wherein said compound is selected from:
- 1-(benzo[d]isoxazol-3-ylmethyl)-3-(4-((4-methylpiperidin-1-yl)methyl)phenyl)urea;
- 1-((5-methylbenzo[d]isoxazol-3-yl)methyl)-3-(4-((4-methylpiperidin-1-yl)methyl)phenyl)urea;
- 1-((5-methylbenzo[d]isoxazol-3-yl)methyl)-3-(3-(trifluoromethyl)phenyl)urea;
- 1-(3-chlorophenyl)-3-(benzo[d]isoxazol-3-ylmethyl)urea;
- 1-(benzo[d]isoxazol-3-ylmethyl)-3-(3-methoxyphenyl)urea;
- methyl 4-(3-(benzo[d]isoxazol-3-ylmethyl)ureido)benzoate;
- 1-(2-methyl-1-oxo-1,2-dihydroisoquinolin-4-yl)-3-(4-((4-methylpiperidin-1-yl)methyl)phenyl)urea; and
- 1-((5-methylbenzo[d]isoxazol-3-yl)methyl)-3-(2-(4-methylpiperazin-1-yl)phenyl)urea;

or a pharmaceutically acceptable salt thereof.

18. The method according to claim 1, wherein the compound is 1-(benzo[d]isoxazol-3-ylmethyl)-3-(4-((4-methylpiperidin-1-yl)methyl)phenyl)urea, or a pharmaceutically acceptable salt thereof.

19. The method according to claim 1, wherein said inflammatory condition is sepsis.

20. The method according to claim 1, wherein said inflammatory condition is chronic joint disease.

21. The method according to claim 1, wherein said inflammatory condition is chronic active gastritis.

22. The method according to claim 1, wherein said inflammatory condition is chronic mucosal inflammation.

* * * * *